US008080649B2

(12) United States Patent
Miyakawa et al.

(10) Patent No.: US 8,080,649 B2
(45) Date of Patent: Dec. 20, 2011

(54) APTAMER AGAINST MIDKINE AND USE THEREOF

(75) Inventors: Shin Miyakawa, Tokyo (JP); Masatoshi Fujiwara, Tokyo (JP); Yoshikazu Nakamura, Tokyo (JP); Takashi Matsui, Abiko (JP); Sadatoshi Sakuma, Yokohama (JP)

(73) Assignee: Ribomic Inc., Tokyo (JP)

( * ) Notice: Subject to any disclaimer, the term of this patent is extended or adjusted under 35 U.S.C. 154(b) by 0 days.

(21) Appl. No.: 12/312,519

(22) PCT Filed: Nov. 14, 2007

(86) PCT No.: PCT/JP2007/072099
§ 371 (c)(1),
(2), (4) Date: Aug. 6, 2009

(87) PCT Pub. No.: WO2008/059877
PCT Pub. Date: May 22, 2008

(65) Prior Publication Data
US 2010/0004432 A1    Jan. 7, 2010

(30) Foreign Application Priority Data
Nov. 14, 2006    (JP) .................................. 2006-308482

(51) Int. Cl.
C07H 21/02    (2006.01)
C07H 21/04    (2006.01)
C12N 15/11    (2006.01)

(52) U.S. Cl. ...................... 536/24.5; 536/23.1; 536/24.3; 536/24.33; 514/44

(58) Field of Classification Search .................. 536/23.1, 536/24.3, 24.33, 24.5
See application file for complete search history.

(56) References Cited

FOREIGN PATENT DOCUMENTS

| | | |
|---|---|---|
| JP | 6-172218 | 6/1994 |
| JP | 2000-354487 | 12/2000 |
| JP | 2004-344008 | 12/2004 |
| JP | 2006-141305 | 6/2006 |
| JP | 2006-211905 | 8/2006 |
| WO | 99/03493 | 1/1999 |
| WO | 00/10608 | 3/2000 |
| WO | 2004/078210 | 9/2004 |
| WO | 2004/085642 | 10/2004 |
| WO | 2006/016571 | 2/2006 |

OTHER PUBLICATIONS

Karl Thiel. Nature Biotechnology, 2004 vol. 22, No. 6, pp. 649-651.*
K. Inoh et al., "Doxorubicin-Conjugated Anti-Midkine Monoclonal Antibody as a Potential Anti-Tumor Drug", Japanese Journal of Clinical Oncology, vol. 36, No. 4, pp. 207-211, 2006.

(Continued)

Primary Examiner — Terra C. Gibbs
(74) Attorney, Agent, or Firm — Wenderoth, Lind & Ponack, L.L.P.

(57) ABSTRACT

Provided is a high-quality aptamer against midkine.
An aptamer possessing an inhibitory activity against midkine; a complex comprising an aptamer possessing a binding activity or inhibitory activity against midkine and a functional substance (for example, affinity substances, substances for labeling, enzymes, drug delivery vehicles, drugs and the like); a pharmaceutical drug, cell migration inhibitor, diagnostic reagent, labeling agent and the like comprising an aptamer possessing a binding activity or inhibitory activity against midkine, or a complex comprising the aptamer and a functional substance; a cell migration inhibitor, a diagnostic reagent, a labeling agent and the like.

15 Claims, 12 Drawing Sheets

OTHER PUBLICATIONS

W. Iwasaki et al., "Solution structure of midkine, a new heparin-binding growth factor", The EMBO Journal, vol. 16, No. 23, pp. 6936-6946, 1997.
K. Kadomatsu et al., "cDNA Cloning and Sequencing of a New Gene Intensely Expressed in Early Differentiation Stages of Embryonal Carcinoma Cells and in Mid-Gestation Period of Mouse Embryogenesis", Biochemical and Biophysical Research Communications, vol. 151, No. 3, pp. 1312-1318, Mar. 30, 1988.
M. Tomomura et al., "A Retinoic Acid-Responsive Gene, MK, Found in the Teratocarcinoma System", The Journal of Biological Chemistry, vol. 265, No. 18, pp. 10765-10770, Jun. 25, 1990.
T. Muramatsu, "Midkine and Pleiotrophin: Two Related Proteins Involved in Development, Survival, Inflammation and Tumorigenesis", J. Biochem., vol. 132, pp. 359-371, 2002.
A. D. Ellington et al., "In vitro selection of RNA molecules that bind specific ligands", Nature, vol. 346, pp. 818-822, Aug. 30, 1990.
C. Tuerk et al., "Systematic Evolution of Ligands by Exponential Enrichment: RNA Ligands to Bacteriophage T4 DNA Polymerase", Science, vol. 249, pp. 505-510, Aug. 3, 1990.
M. Horiba et al., "Neointima formation in a restenosis model is suppressed in midkine-deficient mice", The Journal of Clinical Investigation, vol. 105, No. 4, pp. 489-495, Feb. 2000.
H. B. Zeyneloglu et al., "The effect of monocyte chemotactic protein 1 in intraperitoneal adhesion formation in a mouse model", Am. J. Obstet. Gynecol., vol. 179, pp. 438-443, 1998.
A. Murasugi et al., "Efficient Production of Recombinant Human Pleiotrophin in Yeast, *Pichia pastoris* ", Biosci. Biotechnol. Biochem., vol. 67, No. 10, pp. 2288-2290, 2003.
H. Muramatsu et al., "Purification of Recombinant Midkine and Examination of its Biological Activities: Functional Comparison of New Heparin Binding Factors", Biochemical and Biophysical Research Communications, vol. 177, No. 2, pp. 652-658, Jun. 14, 1991.
H. Muramatsu et al., "Localization of Heparin-Binding, Neurite Outgrowth and Antigenic Regions in Midkine Molecule"; Biochemical and Biophysical Research Communications, vol. 203, No. 2, pp. 1131-1139, Sep. 15, 1994.
K. Inoh et al., "Midkine, a heparin-binding cytokine, plays key roles in intraperitoneal adhesions", Biochemical and Biophysical Research Communications, vol. 317, pp. 108-113, 2004.
J. Hobbs et al., "Polynucleotides Containing 2'-Amino-2'-deoxyribose and 2'-Azido-2'-deoxyribose", Biochemistry, vol. 12, No. 25, pp. 5138-5145, 1973.
Y. Takei et al., "Antisense Oligodeoxynucleotide Targeted Midkine, a Heparin-binding Growth Factor, Suppresses Tumorigenicity of Mouse Rectal Carcinoma Cells", Cancer Research, vol. 61, pp. 8486-8491, Dec. 1, 2001.
H. Muramatsu et al., "Midkine, A Retinoic Acid-Inducible Growth/Differentiation Factor: Immunochemical Evidence for the Function and Distribution", Developmental Biological, vol. 159, pp. 392-402, 1998.
T. Takada et al., "Midkine, A Retinoic Acid-Inducible Heparin-Binding Cytokine in Inflammatory Responses: Chemotactic Activity to Neutrophils and Association with Inflammatory Synovitis", J. Biochem., vol. 122, pp. 453-458, 1997.
N. Maeda et al., "A Receptor-like Protein-Tyrosine Phosphatase PTPε/RPTPβ Binds a Heparin-Binding Growth Factor Midkine", The Journal of Biological Chemistry, vol. 274, No. 18, pp. 12474-12479, Apr. 30, 1999.
M. Qi et al., "Haptotactic Migration Induced by Midkine", The Journal of Biological Chemistry, vol. 276, No. 19, pp. 15868-15875, May 11, 2001.
M. Cotten et al., "2'-O-methyl, 2'-O-ethyl oligoribonucleotides and phosphorothioate oligodeoxyribonucleotides as inhibitors of the in vitro U7 snRNP-dependent mRNA processing event", Nucleic Acids Research, vol. 19, No. 10, pp. 2629-2635, 1991.
B. S. Sproat et al., "New synthetic routes to synthons suitable for 2'-O-allyloligoribonucleotide assembly", Nucleic Acids Research, vol. 19, No. 4, pp. 733-738, 1991.
M. Zuker, "Mfold webe server for nucleic acid folding and hybridization prediction", Nucleic Acids Research, vol. 31, No. 13, pp. 3406-3415, 2003.
A. Murasugi et al., "Production of native recombinant human midkine in the yeast, *Pichia pastoris* ", Protein Expression and Purification, vol. 27, pp. 244-252, 2003.
Supplementary European Search Report dated Oct. 13, 2009 in European Application No. EP 07 83 1829.
Chinese Office Action together with English translation issued Nov. 29, 2010 in corresponding Chinese Application No. 200780042428.0.
Shibata et al., "Nuclear Targeting by the Growth Factor Midkine," Oct. 31, 2002, pp. 6788-6796.

* cited by examiner

SEQUENCE LISTING

<160> NUMBER OF SEQ ID NOS: 76

<210> SEQ ID NO 1
<211> LENGTH: 77
<212> TYPE: RNA
<213> ORGANISM: Artificial
<220> FEATURE:
<223> OTHER INFORMATION: Aptamer to midkine

<400> SEQUENCE: 1
gggagaggag aagaggaaau aguuaagggu gaauuugcga aagcuauuuu agucgcagua    60
gaggacagga augagga    77

<210> SEQ ID NO 2
<211> LENGTH: 77
<212> TYPE: RNA
<213> ORGANISM: Artificial
<220> FEATURE:
<223> OTHER INFORMATION: Aptamer to midkine

<400> SEQUENCE: 2
gggagaggag aagaggaagg acuaaguaag agaacaccgg aaugaaggga cuuacgugua    60
gaggacagga augagga    77

<210> SEQ ID NO 3
<211> LENGTH: 75
<212> TYPE: RNA
<213> ORGANISM: Artificial
<220> FEATURE:
<223> OTHER INFORMATION: Aptamer to midkine

<400> SEQUENCE: 3
gggagaggag aagaggaaag ccuucuaccg aaagugggaa agcacacaua aaucugguag    60
aggacaggaa ugaga    75

```
<210> SEQ ID NO 4
<211> LENGTH: 76
<212> TYPE: RNA
<213> ORGANISM: Artificial
<220> FEATURE:
<223> OTHER INFORMATION: Aptamer to midkine

<400> SEQUENCE: 4
gggagaggag aagaggaacg ugcucuguac gaggaguagc cggaaagaag gcggugugua      60
gaggacagga augaga                                                     76

<210> SEQ ID NO 5
<211> LENGTH: 76
<212> TYPE: RNA
<213> ORGANISM: Artificial
<220> FEATURE:
<223> OTHER INFORMATION: Aptamer to midkine

<400> SEQUENCE: 5
gggagaggag aagaggaagu gugcacaggg guuggugucg ggugcauaca guauaagaua      60
gaggacagga augaga                                                     76

<210> SEQ ID NO 6
<211> LENGTH: 67
<212> TYPE: RNA
<213> ORGANISM: Artificial
<220> FEATURE:
<223> OTHER INFORMATION: Aptamer to midkine

<400> SEQUENCE: 6
gggagaggag aagaggaacg ugcucuguac gaggaguagc cggaaagaag gcggugugua      60
gaggaca                                                               67

<210> SEQ ID NO 7
<211> LENGTH: 64
<212> TYPE: RNA
<213> ORGANISM: Artificial
<220> FEATURE:
<223> OTHER INFORMATION: Aptamer to midkine

<400> SEQUENCE: 7
gggaacgugc ucuguacgag gaguagccgg aaagaaggcg guguguagag gacaggaaug      60
agga                                                                  64

<210> SEQ ID NO 8
<211> LENGTH: 69
<212> TYPE: RNA
<213> ORGANISM: Artificial
<220> FEATURE:
<223> OTHER INFORMATION: Aptamer to midkine

<400> SEQUENCE: 8
gggagaggag aagaggaacg cuguacgagg aguagccgga aagaaggcgg uguguagcag      60
gaaugagga                                                             69

<210> SEQ ID NO 9
<211> LENGTH: 66
<212> TYPE: RNA
<213> ORGANISM: Artificial
<220> FEATURE:
<223> OTHER INFORMATION: Aptamer to midkine
```

<400> SEQUENCE: 9
gggagaggag aagaggaacg ugcucuguac gccggaaaga aggugguguag aggacaggaa       60 ugagga       66

<210> SEQ ID NO 10
<211> LENGTH: 73
<212> TYPE: RNA
<213> ORGANISM: Artificial
<220> FEATURE:
<223> OTHER INFORMATION: Aptamer to midkine

<400> SEQUENCE: 10
gggagaggag aagaggaacg ugcucuguac gaggaguagc cgaaaggcgg uguguagagg       60
acaggaauga gga       73

<210> SEQ ID NO 11
<211> LENGTH: 77
<212> TYPE: RNA
<213> ORGANISM: Artificial
<220> FEATURE:
<223> OTHER INFORMATION: Aptamer to midkine

<400> SEQUENCE: 11
gggagaggag aagaggaacg ugcucugcac gaggaguagc cggaaagaag gcggcgugca       60
gaggacagga augagga       77

<210> SEQ ID NO 12
<211> LENGTH: 58
<212> TYPE: RNA
<213> ORGANISM: Artificial
<220> FEATURE:
<223> OTHER INFORMATION: Aptamer to midkine

<400> SEQUENCE: 12
gggagaggag aagaggaacg cugcacgagg aguagccgga aagaaggcgg cgugcagc       58

<210> SEQ ID NO 13
<211> LENGTH: 50
<212> TYPE: RNA
<213> ORGANISM: Artificial
<220> FEATURE:
<223> OTHER INFORMATION: Aptamer to midkine

<400> SEQUENCE: 13
gggagaggaa cgcugcacga ggaguagccg gaaagaaggc ggcgugcagc       50

<210> SEQ ID NO 14
<211> LENGTH: 54
<212> TYPE: RNA
<213> ORGANISM: Artificial
<220> FEATURE:
<223> OTHER INFORMATION: Aptamer to midkine

<400> SEQUENCE: 14
gggagaggag aagaggaacg cuacgaggag uagccggaaa gaaggcggcg uagc       54

<210> SEQ ID NO 15
<211> LENGTH: 56
<212> TYPE: RNA
<213> ORGANISM: Artificial
<220> FEATURE:
<223> OTHER INFORMATION: Aptamer to midkine -continued

<400> SEQUENCE: 15
gggagaggag aagaggaacg cugcacgagg aguagccgga aagggcggcg ugcagc          56

<210> SEQ ID NO 16
<211> LENGTH: 57
<212> TYPE: RNA
<213> ORGANISM: Artificial
<220> FEATURE:
<223> OTHER INFORMATION: Aptamer to midkine

<400> SEQUENCE: 16
gggagaggag aagaggaacg cugcacgagg guagccggaa agaaggcggc gugcagc         57

<210> SEQ ID NO 17
<211> LENGTH: 46
<212> TYPE: RNA
<213> ORGANISM: Artificial
<220> FEATURE:
<223> OTHER INFORMATION: Aptamer to midkine

<400> SEQUENCE: 17
gggagaggaa cgcuacgagg aguagccgga aagaaggcgg cguagc                    46

<210> SEQ ID NO 18
<211> LENGTH: 37
<212> TYPE: RNA
<213> ORGANISM: Artificial
<220> FEATURE:
<223> OTHER INFORMATION: Aptamer to midkine

<400> SEQUENCE: 18
gggcuacgag gaguagccgg aaagaaggcg gcguagc                              37

<210> SEQ ID NO 19
<211> LENGTH: 44
<212> TYPE: RNA
<213> ORGANISM: Artificial
<220> FEATURE:
<223> OTHER INFORMATION: Aptamer to midkine

<400> SEQUENCE: 19
gggagaggaa cguacgagga guagccggaa agaaggcggc guac                      44

<210> SEQ ID NO 20
<211> LENGTH: 42
<212> TYPE: RNA
<213> ORGANISM: Artificial
<220> FEATURE:
<223> OTHER INFORMATION: Aptamer to midkine

<400> SEQUENCE: 20
gggagaggaa cgacgaggag uagccggaaa gaaggcggcg uc                        42

<210> SEQ ID NO 21
<211> LENGTH: 44
<212> TYPE: RNA
<213> ORGANISM: Artificial
<220> FEATURE:
<223> OTHER INFORMATION: Aptamer to midkine

<400> SEQUENCE: 21
gggagaggaa cgcuacgagg aguagcggaa agaagcggcg uagc                      44

```
<210> SEQ ID NO 22
<211> LENGTH: 33
<212> TYPE: RNA
<213> ORGANISM: Artificial
<220> FEATURE:
<223> OTHER INFORMATION: Aptamer to midkine

<400> SEQUENCE: 22
gggacgagga guagccggaa agaaggcggc guc                                    33

<210> SEQ ID NO 23
<211> LENGTH: 38
<212> TYPE: RNA
<213> ORGANISM: Artificial
<220> FEATURE:
<223> OTHER INFORMATION: Aptamer to midkine

<400> SEQUENCE: 23
gggagaggaa cgacgaggag uagccgaaag gcggcguc                               38

<210> SEQ ID NO 24
<211> LENGTH: 38
<212> TYPE: RNA
<213> ORGANISM: Artificial
<220> FEATURE:
<223> OTHER INFORMATION: Aptamer to midkine

<400> SEQUENCE: 24
gggagaggaa cgacgaggag uagccuucgg gcggcguc                               38

<210> SEQ ID NO 25
<211> LENGTH: 41
<212> TYPE: RNA
<213> ORGANISM: Artificial
<220> FEATURE:
<223> OTHER INFORMATION: Aptamer to midkine

<400> SEQUENCE: 25
gggagaggaa cgacgagaac agccggaaag aaggcggcgu c                           41

<210> SEQ ID NO 26
<211> LENGTH: 41
<212> TYPE: RNA
<213> ORGANISM: Artificial
<220> FEATURE:
<223> OTHER INFORMATION: Aptamer to midkine

<400> SEQUENCE: 26
gggagaggaa cgacgagagu agccggaaag aaggcggcgu c                           41

<210> SEQ ID NO 27
<211> LENGTH: 41
<212> TYPE: RNA
<213> ORGANISM: Artificial
<220> FEATURE:
<223> OTHER INFORMATION: Aptamer to midkine

<400> SEQUENCE: 27
gggagaggaa cgacgagggu agccggaaag aaggcggcgu c                           41

<210> SEQ ID NO 28
<211> LENGTH: 31
<212> TYPE: RNA
<213> ORGANISM: Artificial
<220> FEATURE:
<223> OTHER INFORMATION: Aptamer to midkine
```

```
<400> SEQUENCE: 28
ggcgaggagu agccggaaag aaggcggcgc c                              31

<210> SEQ ID NO 29
<211> LENGTH: 31
<212> TYPE: RNA
<213> ORGANISM: Artificial
<220> FEATURE:
<223> OTHER INFORMATION: Aptamer to midkine

<400> SEQUENCE: 29
gacgaggagu agccggaaag aaggcggcgu c                              31

<210> SEQ ID NO 30
<211> LENGTH: 71
<212> TYPE: RNA
<213> ORGANISM: Artificial
<220> FEATURE:
<223> OTHER INFORMATION: Aptamer to midkine

<400> SEQUENCE: 30
ggagaagagg aagugugcac aggggutuggu gucgggugca uacaguauaa gauagaggac     60
aggaaugagg a                                                          71

<210> SEQ ID NO 31
<211> LENGTH: 67
<212> TYPE: RNA
<213> ORGANISM: Artificial
<220> FEATURE:
<223> OTHER INFORMATION: Aptamer to midkine

<400> SEQUENCE: 31
gggagaggag aagaggaagu gugcacaggg guuggugucg ggugcauaca guauaagaua     60
gaggaca                                                              67

<210> SEQ ID NO 32
<211> LENGTH: 57
<212> TYPE: RNA
<213> ORGANISM: Artificial
<220> FEATURE:
<223> OTHER INFORMATION: Aptamer to midkine

<400> SEQUENCE: 32
gggagaggag aagaggaagu gugcacaggg guuggugucg ggugcauaca guauaag        57

<210> SEQ ID NO 33
<211> LENGTH: 61
<212> TYPE: RNA
<213> ORGANISM: Artificial
<220> FEATURE:
<223> OTHER INFORMATION: Aptamer to midkine

<400> SEQUENCE: 33
ggagaagagg aagugugcac aggggutuggu gucgggugca uacaguauaa gauagaggac     60
a                                                                    61

<210> SEQ ID NO 34
<211> LENGTH: 46
<212> TYPE: RNA
<213> ORGANISM: Artificial
<220> FEATURE:
<223> OTHER INFORMATION: Aptamer to midkine
```

```
<400> SEQUENCE: 34
ggaggaagug ugcacagggg uuggugucgg gugcauacag uauaag            46

<210> SEQ ID NO 35
<211> LENGTH: 51
<212> TYPE: RNA
<213> ORGANISM: Artificial
<220> FEATURE:
<223> OTHER INFORMATION: Aptamer to midkine

<400> SEQUENCE: 35
gggagaggag aagaggaagu gugcacaggg guuggugucg ggugcauaca g      51

<210> SEQ ID NO 36
<211> LENGTH: 53
<212> TYPE: RNA
<213> ORGANISM: Artificial
<220> FEATURE:
<223> OTHER INFORMATION: Aptamer to midkine

<400> SEQUENCE: 36
gggagaggag aagaggaagu gcacaggggu uggugucggg ugcacaguau aag    53

<210> SEQ ID NO 37
<211> LENGTH: 49
<212> TYPE: RNA
<213> ORGANISM: Artificial
<220> FEATURE:
<223> OTHER INFORMATION: Aptamer to midkine

<400> SEQUENCE: 37
gggagaggag aagaggaagc acagggguug gugucggguc caguauaag         49

<210> SEQ ID NO 38
<211> LENGTH: 57
<212> TYPE: RNA
<213> ORGANISM: Artificial
<220> FEATURE:
<223> OTHER INFORMATION: Aptamer to midkine

<400> SEQUENCE: 38
ggguuuuuuu uuuuuuugu gugcacaggg guuggugucg ggugcauaca guauaag  57

<210> SEQ ID NO 39
<211> LENGTH: 45
<212> TYPE: RNA
<213> ORGANISM: Artificial
<220> FEATURE:
<223> OTHER INFORMATION: Aptamer to midkine

<400> SEQUENCE: 39
gggagaggag aagaggaagg cacagggguu ggugucgggu gccag             45

<210> SEQ ID NO 40
<211> LENGTH: 49
<212> TYPE: RNA
<213> ORGANISM: Artificial
<220> FEATURE:
<223> OTHER INFORMATION: Aptamer to midkine

<400> SEQUENCE: 40
gggagaggag aagaggaagu gugcacaggg guuggugucg ggugcauac         49
```

```
<210> SEQ ID NO 41
<211> LENGTH: 52
<212> TYPE: RNA
<213> ORGANISM: Artificial
<220> FEATURE:
<223> OTHER INFORMATION: Aptamer to midkine

<400> SEQUENCE: 41
gggaaggaga agaggaagug cacaggggguu ggugucgggu gcacaguaua ag       52

<210> SEQ ID NO 42
<211> LENGTH: 52
<212> TYPE: RNA
<213> ORGANISM: Artificial
<220> FEATURE:
<223> OTHER INFORMATION: Aptamer to midkine

<400> SEQUENCE: 42
gggagaggag agaggaagug cacaggggguu ggugucgggu gcacaguaua ag       52

<210> SEQ ID NO 43
<211> LENGTH: 52
<212> TYPE: RNA
<213> ORGANISM: Artificial
<220> FEATURE:
<223> OTHER INFORMATION: Aptamer to midkine

<400> SEQUENCE: 43
gggagaggag aagaggagug cacaggggguu ggugucgggu gcacaguaua ag       52

<210> SEQ ID NO 44
<211> LENGTH: 47
<212> TYPE: RNA
<213> ORGANISM: Artificial
<220> FEATURE:
<223> OTHER INFORMATION: Aptamer to midkine

<400> SEQUENCE: 44
gggagaggag aagaggaagu ugcacagggg uuggugucgg gugcaac             47

<210> SEQ ID NO 45
<211> LENGTH: 45
<212> TYPE: RNA
<213> ORGANISM: Artificial
<220> FEATURE:
<223> OTHER INFORMATION: Aptamer to midkine

<400> SEQUENCE: 45
gggagaggag aagaggaagu gcacaggggu uggugucggg ugcac               45

<210> SEQ ID NO 46
<211> LENGTH: 49
<212> TYPE: RNA
<213> ORGANISM: Artificial
<220> FEATURE:
<223> OTHER INFORMATION: Aptamer to midkine

<400> SEQUENCE: 46
gggagaggag aagaggaagu gcgcgcaggg guuggugucg ggcgcguac           49

<210> SEQ ID NO 47
<211> LENGTH: 48
<212> TYPE: RNA
<213> ORGANISM: Artificial
<220> FEATURE:
<223> OTHER INFORMATION: Aptamer to midkine
```

```
<400> SEQUENCE: 47
gggagaggag aagaggaagu gugcacaggg guggugucgg gugcauac          48

<210> SEQ ID NO 48
<211> LENGTH: 48
<212> TYPE: RNA
<213> ORGANISM: Artificial
<220> FEATURE:
<223> OTHER INFORMATION: Aptamer to midkine

<400> SEQUENCE: 48
gggagaggag aagaggaagu gugcacaggg guugugucgg gugcauac          48

<210> SEQ ID NO 49
<211> LENGTH: 48
<212> TYPE: RNA
<213> ORGANISM: Artificial
<220> FEATURE:
<223> OTHER INFORMATION: Aptamer to midkine

<400> SEQUENCE: 49
gggagaggag aagaggaagu gugcacaggg guugggucgg gugcauac          48

<210> SEQ ID NO 50
<211> LENGTH: 43
<212> TYPE: RNA
<213> ORGANISM: Artificial
<220> FEATURE:
<223> OTHER INFORMATION: Aptamer to midkine

<400> SEQUENCE: 50
gggaaggaaa gaggaagugc acagggguug gugucgggug cac               43

<210> SEQ ID NO 51
<211> LENGTH: 51
<212> TYPE: RNA
<213> ORGANISM: Artificial
<220> FEATURE:
<223> OTHER INFORMATION: Aptamer to midkine

<400> SEQUENCE: 51
gggaaggaga gaggaagugc acagggguug gugucgggug cacaguauaa g      51

<210> SEQ ID NO 52
<211> LENGTH: 51
<212> TYPE: RNA
<213> ORGANISM: Artificial
<220> FEATURE:
<223> OTHER INFORMATION: Aptamer to midkine

<400> SEQUENCE: 52
ggaaggagaa gaggaagugc acagggguug gugucgggug cacaguauaa g      51

<210> SEQ ID NO 53
<211> LENGTH: 51
<212> TYPE: RNA
<213> ORGANISM: Artificial
<220> FEATURE:
<223> OTHER INFORMATION: Aptamer to midkine

<400> SEQUENCE: 53
gggaaggaaa gaggaagugc acagggguug gugucgggug cacaguauaa g      51
```

```
<210> SEQ ID NO 54
<211> LENGTH: 45
<212> TYPE: RNA
<213> ORGANISM: Artificial
<220> FEATURE:
<223> OTHER INFORMATION: Aptamer to midkine

<400> SEQUENCE: 54
gggagaggag aagaggaagu gcacaggggu uggugucggg ugcac          45

<210> SEQ ID NO 55
<211> LENGTH: 43
<212> TYPE: RNA
<213> ORGANISM: Artificial
<220> FEATURE:
<223> OTHER INFORMATION: Aptamer to midkine

<400> SEQUENCE: 55
gggagaggag gaggaagugc acagggguug gugucggguo cac            43

<210> SEQ ID NO 56
<211> LENGTH: 43
<212> TYPE: RNA
<213> ORGANISM: Artificial
<220> FEATURE:
<223> OTHER INFORMATION: Aptamer to midkine

<400> SEQUENCE: 56
gggagaggag aaggaagugc acagggguug gugucggguo cac            43

<210> SEQ ID NO 57
<211> LENGTH: 43
<212> TYPE: RNA
<213> ORGANISM: Artificial
<220> FEATURE:
<223> OTHER INFORMATION: Aptamer to midkine

<400> SEQUENCE: 57
gggagaggag aagaaagugc acagggguug gugucggguo cac            43

<210> SEQ ID NO 58
<211> LENGTH: 43
<212> TYPE: RNA
<213> ORGANISM: Artificial
<220> FEATURE:
<223> OTHER INFORMATION: Aptamer to midkine

<400> SEQUENCE: 58
gggagaggag aagagggugc acagggguug gugucggguo cac            43

<210> SEQ ID NO 59
<211> LENGTH: 29
<212> TYPE: RNA
<213> ORGANISM: Artificial
<220> FEATURE:
<223> OTHER INFORMATION: Aptamer to midkine

<400> SEQUENCE: 59
gggugcacag ggguuggugu cgggugcac                            29

<210> SEQ ID NO 60
<211> LENGTH: 35
<212> TYPE: RNA
<213> ORGANISM: Artificial
<220> FEATURE:
<223> OTHER INFORMATION: Aptamer to midkine
```

```
<400> SEQUENCE: 60
gggaaggagu gcacaggggu uggugucggg ugcac                              35

<210> SEQ ID NO 61
<211> LENGTH: 39
<212> TYPE: RNA
<213> ORGANISM: Artificial
<220> FEATURE:
<223> OTHER INFORMATION: Aptamer to midkine

<400> SEQUENCE: 61
gggaaggagg aagugcacag gggu uggugu cgggugcac                         39

<210> SEQ ID NO 62
<211> LENGTH: 39
<212> TYPE: RNA
<213> ORGANISM: Artificial
<220> FEATURE:
<223> OTHER INFORMATION: Aptamer to midkine

<400> SEQUENCE: 62
gggagaggag aagugcacag gggu uggugu cgggugcac                         39

<210> SEQ ID NO 63
<211> LENGTH: 45
<212> TYPE: RNA
<213> ORGANISM: Artificial
<220> FEATURE:
<223> OTHER INFORMATION: Aptamer to midkine

<400> SEQUENCE: 63
gggagaggag aagaggaagu gcacccgggu uggugucggg ugcac                   45

<210> SEQ ID NO 64
<211> LENGTH: 37
<212> TYPE: RNA
<213> ORGANISM: Artificial
<220> FEATURE:
<223> OTHER INFORMATION: Aptamer to midkine

<400> SEQUENCE: 64
gggaaggagg aaggcacagg gguuggguc gggugcc                             37

<210> SEQ ID NO 65
<211> LENGTH: 39
<212> TYPE: RNA
<213> ORGANISM: Artificial
<220> FEATURE:
<223> OTHER INFORMATION: Aptamer to midkine

<400> SEQUENCE: 65
gggaaggagg aagugcaccc ggguugguguc gggugcac                          39

<210> SEQ ID NO 66
<211> LENGTH: 38
<212> TYPE: RNA
<213> ORGANISM: Artificial
<220> FEATURE:
<223> OTHER INFORMATION: Aptamer to midkine

<400> SEQUENCE: 66
ggaaggagga agugcacagg gguuggguguc gggugcac                          38
```

```
<210> SEQ ID NO 67
<211> LENGTH: 38
<212> TYPE: RNA
<213> ORGANISM: Artificial
<220> FEATURE:
<223> OTHER INFORMATION: Aptamer to midkine

<400> SEQUENCE: 67
ggaaggagga agugcacagg gguugguguc gggugcac                            38

<210> SEQ ID NO 68
<211> LENGTH: 39
<212> TYPE: RNA
<213> ORGANISM: Artificial
<220> FEATURE:
<223> OTHER INFORMATION: Aptamer to midkine

<400> SEQUENCE: 68
gggaaggagg aagugcacag ggguuggagu cgggugcac                           39

<210> SEQ ID NO 69
<211> LENGTH: 39
<212> TYPE: RNA
<213> ORGANISM: Artificial
<220> FEATURE:
<223> OTHER INFORMATION: Aptamer to midkine

<400> SEQUENCE: 69
gggaaggagg aagugcacag gggauggugu cgggugcac                           39

<210> SEQ ID NO 70
<211> LENGTH: 39
<212> TYPE: RNA
<213> ORGANISM: Artificial
<220> FEATURE:
<223> OTHER INFORMATION: Aptamer to midkine

<400> SEQUENCE: 70
gggaaggagg aagugcacag gggauggugu cgggugcac                           39

<210> SEQ ID NO 71
<211> LENGTH: 77
<212> TYPE: DNA
<213> ORGANISM: Artificial
<220> FEATURE:
<223> OTHER INFORMATION: DNA template for producing aptamer to midkine
<220> FEATURE:
<221> NAME/KEY: misc_feature
<223> OTHER INFORMATION: n is a, c, g or t
<220> FEATURE:
<221> NAME/KEY: misc_feature
<222> LOCATION: (20)..(59)
<223> OTHER INFORMATION: n is a, c, g, or t

<400> SEQUENCE: 71
tcctcattcc tgtcctctan nnnnnnnnnn nnnnnnnnnn nnnnnnnnnn nnnnnnnnt     60 tcctcttctc ctctccc                                                   77

<210> SEQ ID NO 72
<211> LENGTH: 35
<212> TYPE: DNA
<213> ORGANISM: Artificial
<220> FEATURE:
<223> OTHER INFORMATION: primer for producing aptamer to midkine

<400> SEQUENCE: 72
taatacgact cactataggg agaggagaag aggaa                               35
```

```
<210> SEQ ID NO 73
<211> LENGTH: 19
<212> TYPE: DNA
<213> ORGANISM: Artificial
<220> FEATURE:
<223> OTHER INFORMATION: reverse primer for producing aptamer to
      midkine

<400> SEQUENCE: 73
tcctcattcc tgtcctcta                                              19

<210> SEQ ID NO 74
<211> LENGTH: 33
<212> TYPE: DNA
<213> ORGANISM: Artificial
<220> FEATURE:
<223> OTHER INFORMATION: DNA aptamer to thrombin (Thrombin-S)

<400> SEQUENCE: 74
tggttggtgt ggttggtaaa aaaaaaaaaa aaa                              33

<210> SEQ ID NO 75
<211> LENGTH: 17
<212> TYPE: DNA
<213> ORGANISM: Artificial
<220> FEATURE:
<223> OTHER INFORMATION: DNA aptamer to HIV (HIV-S)

<400> SEQUENCE: 75
gtggtgggtg ggtgggt                                                17

<210> SEQ ID NO 76
<211> LENGTH: 49
<212> TYPE: RNA
<213> ORGANISM: Artificial
<220> FEATURE:
<223> OTHER INFORMATION: Aptamer to midkine

<400> SEQUENCE: 76
gggagaggag aagaggaagu gugcacaggg guuggugucg ggugcauac             49
```

APTAMER AGAINST MIDKINE AND USE THEREOF

This application is a U.S. national stage of International Application No. PCT/JP2007/072099 filed Nov. 14, 2007.

TECHNICAL FIELD

The present invention relates to an aptamer against midkine, a method of utilizing the same and the like.

BACKGROUND OF THE INVENTION

Midkine (hereinafter abbreviated as "MK" as required) is a growth/differentiation factor that was first discovered as a gene product expressed transiently in the process of differentiation induction of embyonic tumor cells (EC) with retinoic acid, being a polypeptide having a molecular weight of 13 kDa, rich in basic amino acids and cysteine (see, for example, non-patent document 1 and non-patent document 2).

The steric structure of MK has been determined by NMR and reported (see, for example, non-patent document 3). When characterized structurally, MK is configured mainly with two domains. Specifically, MK consists of a fragment on the N-terminal side consisting of amino acid residues 1 to 52 (hereinafter referred to as "the N-terminal fragment"), a fragment on the C-terminal side consisting of amino acid residues 62 to 121 (hereinafter referred to as "the C-terminal fragment") and a loop region that connects the fragments (amino acid residues 53 to 61). Bound to the outside of each domain is a tail that is rich in basic amino acids. In the MK molecule, each of the N-terminal fragment and the C-terminal fragment has a steric structure consisting mainly of three reversed β sheet structures (hereinafter referred to as "domains"; a domain consisting of the amino acid residues 15 to 52 in the N-terminal fragment referred to as "the N-domain", a domain consisting of the amino acid residue 62 to 104 in the C-terminal fragment referred to as "the C-domain"), and freely moving structures assuming no particular structure (hereinafter referred to as "tails"; a tail consisting of the amino acid resideues 1 to 14 in the N-terminal fragment referred to as "the N-tail", and a tail consisting of the amino acid resigues 105-121 in the C-terminal fragment referred to as "the C-tail").

Known receptors of MK include receptor-type protein tyrosine phosphatase ζ (PTPζ), LRP (low density lipoprotein receptor-related protein), ALK (anaplastic leukemia kinase), integrin and syndecan and the like. MK is a highly positively charged protein containing large amounts of the basic amino acids lysine (K) and arginine (R). It has a heparin-binding site in the C-domain thereof, and is known to bind strongly to negatively charged molecules such as heparin and chondroitin sulfate E. As a result of mutagenesis analysis and NMR analysis, it is thought that cluster I, configured with K79, R81, and K102, and cluster II, configured with K86, K87, and R89, are important to the binding with heparin. Meanwhile, a report that only cluster I is important to the binding with chondroitin sulfate E is available. When R81 of cluster I is replaced with A, the binding activity with heparin decreases. As a result, the reduction of the binding activity to PTPζ and the MK-induced neurite elongation and movement of nerve cells are suppressed.

Some growth factors such as fibroblast growth factor (bFGF) and vascular endothelial cell growth factor (VEGF) have a heparin-binding site. These growth factors are thought to bind to heparan sulfate proteoglycan, an extracellular matrix, stay at appropriate positions, and are released as required. The same are also known to bind to heparan sulfate expressed in nerve cells and vascular endothelial cells to contribute to neurite elongation and fibrinolytic activity elevation. When a Petri dish is coated with MK and mouse embryo nerve cells are sown thereon, neurites elongate. In this situation, digestion of the nerve cells with heparitinase suppresses the neurite elongation. Meanwhile, when vascular endothelial cells are cultured and MK is added, the plasminogen Activator activity of the cells rises. In this case as well, digestion of the cells with heparitinase suppresses the elevation of plasminogen activity.

MK is thought to be bound with PTPζ at two sites. One site involves a high affinity bond with chondroitin sulfate (Kd=0.58 nM). This bond disappears upon digestion with chondroitinase. The other site involves a bond with protein, being a low-affinity bond that remains after digestion with chondroitinase (Kd=3 nM). MK promotes the migration of fetal nerve cells expressing PTPζ; treatment of the nerve cells with chondroitinase ABC suppresses the migration. Osteoblast-like UMR106 cells are expressing PTPζ, and are known to have the MK-dependent migration thereof suppressed by treatment with chondroitinase ABC. The MK-dependent migration of macrophage is also suppressed by treatment with chondroitinase ABC, chondroitinase B, or heparinase. Because macrophage is not thought to express PTPζ, is it thought that another receptor is involved.

Whatever negatively charged does not bind to the heparin-binding site of MK. When. MK was immobilized by aminocoupling and subjected to surface plasmon resonance analysis, the results obtained showed that chondroitin sulfate E and heparin bound strongly to MK, whereas chondroitin sulfate A, B, C, and D did not bind thereto.

MK is known to possess a broad range of biological activities. For example, it is known that in human cancer cells, the expression of MK is increased. This increased expression has been observed in a wide variety of cancers, including esophageal cancer, thyroid cancer, urinary bladder cancer, colorectal cancer, gastric cancer, pancreatic cancer, chest cancer, liver cancer, lung cancer, breast cancer, neuroblastoma, glioblastoma, uterine cancer, ovarian cancer, and Wilms' tumor (see, for example, patent document 1 and non-patent document 4). MK is also thought to promote the survival and movement of cancer cells and facilitate neovascularization to help the advancement of cancer.

MK is also known to be one of the molecules that play the central role in the process of development of inflammation. For example, it is known that the formation of nascent intima after blood vessel damage and the onset of nephritis in ischemic injury are mitigated in knockout mice lacking the MK gene. It is also known that in a rheumatism model, postoperative adhesion is also considerably mitigated in MK knockout mice (see, for example, patent document 2, patent document 3 and patent document 4). Hence, MK is known to be involved in inflammatory diseases such as arthritis, autoimmune disease, rheumatic arthritis (rheumatoid arthritis (RA), osteoarthritis (OA)), multiple sclerosis, postoperative adhesion, inflammatory colitis, psoriasis, lupus, asthma, and neutrophil functional abnormalities. Furthermore, MK is known to promote the movement (migration) of inflammatory cells such as macrophage and neutrophils. Because this movement is required for the development of inflammation, it is thought that when midkine is lacked, inflammation-based diseases are unlikely to occur. (See, for example, patent document 5).

Since MK levels are increased in the peritoneal fluid of females with advanced endometriosis, and also since MK stimulates the proliferation of cultured endometrial interstitial cells, MK is known to be involved in the onset and progression of endometriosis (see, for example, patent document 6).

Furthermore, exhibiting vascular intimal thickening action, MK is known to be involved in vascular obstructive diseases such as restenosis following vascular reconstruction surgery, cardiac coronary arterial vascular obstructive disease, cerebral vascular obstructive disease, renal vascular obstructive disease, peripheral vascular obstructive disease, arteriosclerosis, and cerebral infarction (see, for example, patent document 2).

Cell migration is known to be important to the mechanisms for cancer cell infiltration/metastasis, intimal thickening in arteriosclerotic foci, neovascularization and the like. It is also known that inflammatory cell migration is profoundly associated with cardiovascular diseases such as angina pectoris, myocardial infarction, cerebral infarction, cerebral hemorrhage, and hypertension.

Pleiotrophin (PTN or HB-GAM) is the only family protein of the MK, having approximately 50% homology to MK. Both MK and PTN are proteins containing large amounts of cysteine and basic residues. All the 10 cysteine residues are conserved in MK and PTN, and structurally, both can be divided into the N-domain and the C-domain. As a result of NMR analysis, it is known that these two molecules have very similar three-dimensional structures. Each domain consists of three β sheets, connected via a flexible linker region. K79, R81, and K102, considered to be important to the binding with chondroitin sulfate and heparin, are conserved between the two proteins. K79 and R81 are present on the same β sheet, whereas K102 is present on another β sheet. When MK and PTN form a steric structure, these basic residues appear in the vicinity of the protein surface.

In recent years, applications of RNA aptamers to therapeutic drugs, diagnostic reagents, and test reagents have been drawing attention; some RNA aptamers have already been in clinical stage or in practical stage. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX (Systematic Evolution of Ligands by Exponential Enrichment) method (non-patent documents 5, 6). The SELEX method is a method by which an RNA that binds specifically to a target substance is selected from about $10^{14}$ RNA pools having different nucleotide sequences. The RNA used has a structure wherein a random sequence of about 40 residues is sandwiched by primer sequences. This RNA pools are allowed to associate with a target substance, and only the RNA that has bound to the target substance is recovered using a filter and the like. The RNA recovered is amplified by RT-PCR, and this is used as the template for the next round. By repeating this operation about 10 times, an RNA aptamer that binds specifically to the target substance can be sometimes acquired.

[patent document 1] JP-A-6-172218
[patent document 2] WO2000/10608
[patent document 3] WO2004/078210
[patent document 4] WO2004/085642
[patent document 5] WO1999/03493
[patent document 6] WO2006/016571
[non-patent document 1] Kadomatsu, K. et al., Biochem. Biophys. Res. Commun., 151:p. 1312-1318
[non-patent document 2] Tomokura, M. et al., J. Biol. Chem, 265: p. 10765-10770
[non-patent document 3] Iwasaki, W. et al., (1997) EMBO J. 16, p. 6936-6946
[non-patent document 4] Muramatsu, T., (2002) J. Biochem. 132, p. 359-371
[non-patent document 5] Ellington et al., (1990) Nature, 346, 818-822
[non-patent document 6] Tuerk et al., (1990) Science, 249, 505-510

DISCLOSURE OF THE INVENTION

Problems to be Solved by the Invention

The present invention is directed to providing an aptamer for midkine and a method for utilizing the same, and the like.

Means of Solving the Problems

The present inventors investigated diligently to solve the problem described above, and, as a result, succeeded in preparing an aptamer of good quality for midkine, which resulted in the completion of the present invention.

Accordingly, the present invention provides the following:
[1] an aptamer possessing an inhibitory activity against midkine,
[2] the aptamer of [1], wherein the aptamer does not possess an inhibitory activity against pleiotrophin,
[3] the aptamer of [1], possessing a binding activity to the N-terminal fragment of midkine,
[4] the aptamer of [1], possessing a binding activity to the C-terminal fragment of midkine,
[5] the aptamer of [2], possessing a binding activity to the N-terminal fragment of midkine,
[6] the aptamer of [2], possessing a binding activity to the C-terminal fragment of midkine,
[7] an aptamer that exhibits an inhibitory activity against midkine by inhibiting the binding of midkine and PTPζ,
[8] the aptamer of [1], which is either (a) or (b) below:
(a) an aptamer comprising a nucleotide sequence selected from among SEQ ID NO:1 to 70 (with the provision that the uracil may be thymine), wherein the nucleotides contained in the aptamer are such that,
  (i) the 2'-positions of the pyrimidine nucleotides, whether identical or different, are fluorine atoms or substituted by atoms or groups selected from the group consisting of hydrogen atoms, hydroxy groups and methoxy groups, and
  (ii) the 2'-positions of the purine nucleotides, whether identical or different, are hydroxy groups or substituted by atoms or groups selected from the group consisting of hydrogen atoms, methoxy groups and fluorine atoms;
(b) an aptamer comprising a nucleotide sequence selected from among SEQ ID NO:1 to 70 (with the provision that the uracil may be thymine), wherein one or several nucleotides are substituted, deleted, inserted or added, wherein the nucleotides contained in the aptamer are such that,
  (i) the 2'-positions of the pyrimidine nucleotides, whether identical or different, are fluorine atoms or substituted by atoms or groups selected from the group consisting of hydrogen atoms, hydroxy groups and methoxy groups, and
  (ii) the 2'-positions of the purine nucleotides, whether identical or different, are hydroxy groups or substituted by atoms or groups selected from the group consisting of hydrogen atoms, methoxy groups and fluorine atoms,
[9] the aptamer of any one of [1] to [8], wherein an nucleotide contained in the aptamer is modified,
[10] a complex comprising the aptamer of any one of [1] to [9] and a functional substance,

[11] the complex of [10], wherein the functional substance is an affinity substance, a substance for labeling, an enzyme, a drug delivery vehicle or a drug.

[12] a pharmaceutical drug comprising the aptamer of any one of [1] to [9] or the complex of [10] or [11],

[13] a cell migration inhibitor comprising the aptamer of any one of [1] to [9] or the complex of [10] or [11],

[14] a diagnostic reagent comprising the aptamer of any one of [1] to [9] or the complex of [10] or [11],

[15] a labeling agent comprising the aptamer of any one of [1] to [9] or the complex of [10] or [11], and

[16] a method of detecting the aptamer of any one of [1] to [9] or the complex of [10] or [11].

EFFECT OF THE INVENTION

The aptamer or the complex of the present invention can be useful as pharmaceutical drugs or reagents such as diagnostic reagents, for various diseases such as autoimmune disease, cancer, postoperative adhesion, and endometriosis. The aptamer or the complex of the present invention can also be useful in purifying and concentrating MK, and detecting and quantifying MK.

BEST MODE FOR EMBODYING THE INVENTION

Figure 1A:
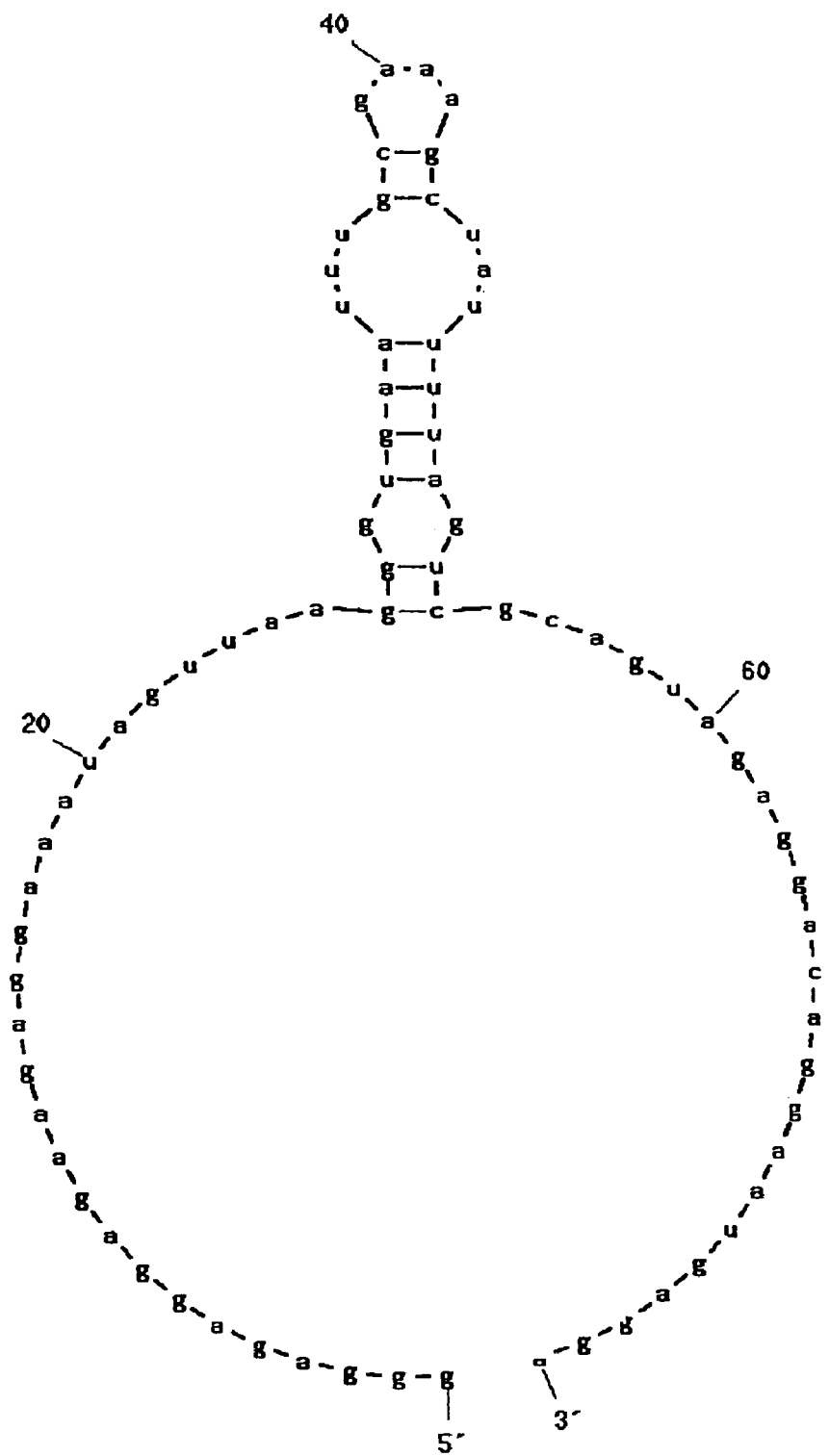
FIG. 1A shows one of the two secondary structures of RNA shown by SEQ ID NO:1 predicted by the MFOLD program.
Figure 1B:
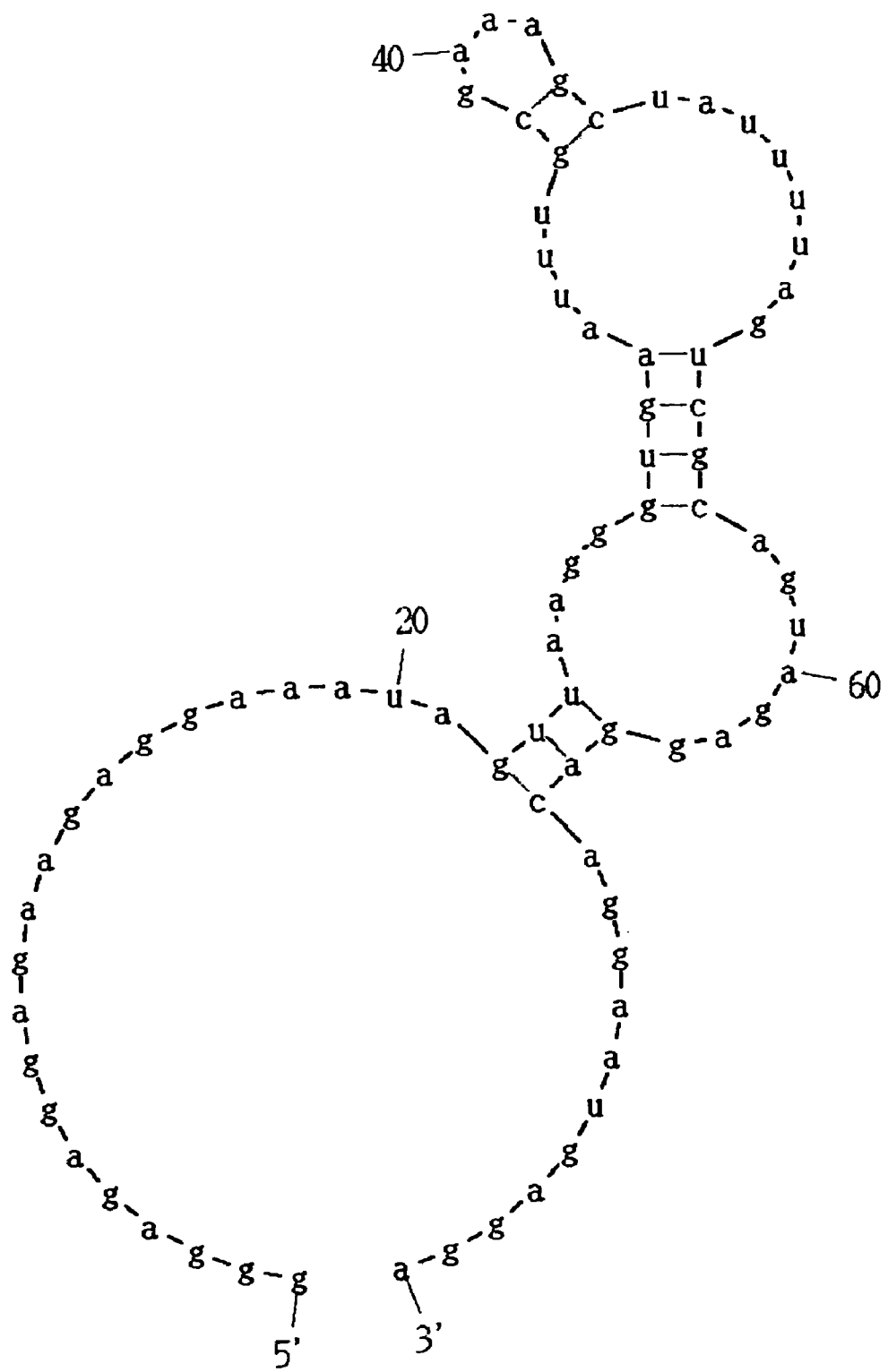
FIG. 1B shows the other secondary structure of RNA shown by SEQ ID NO:1 predicted by the MFOLD program.
Figure 2A:
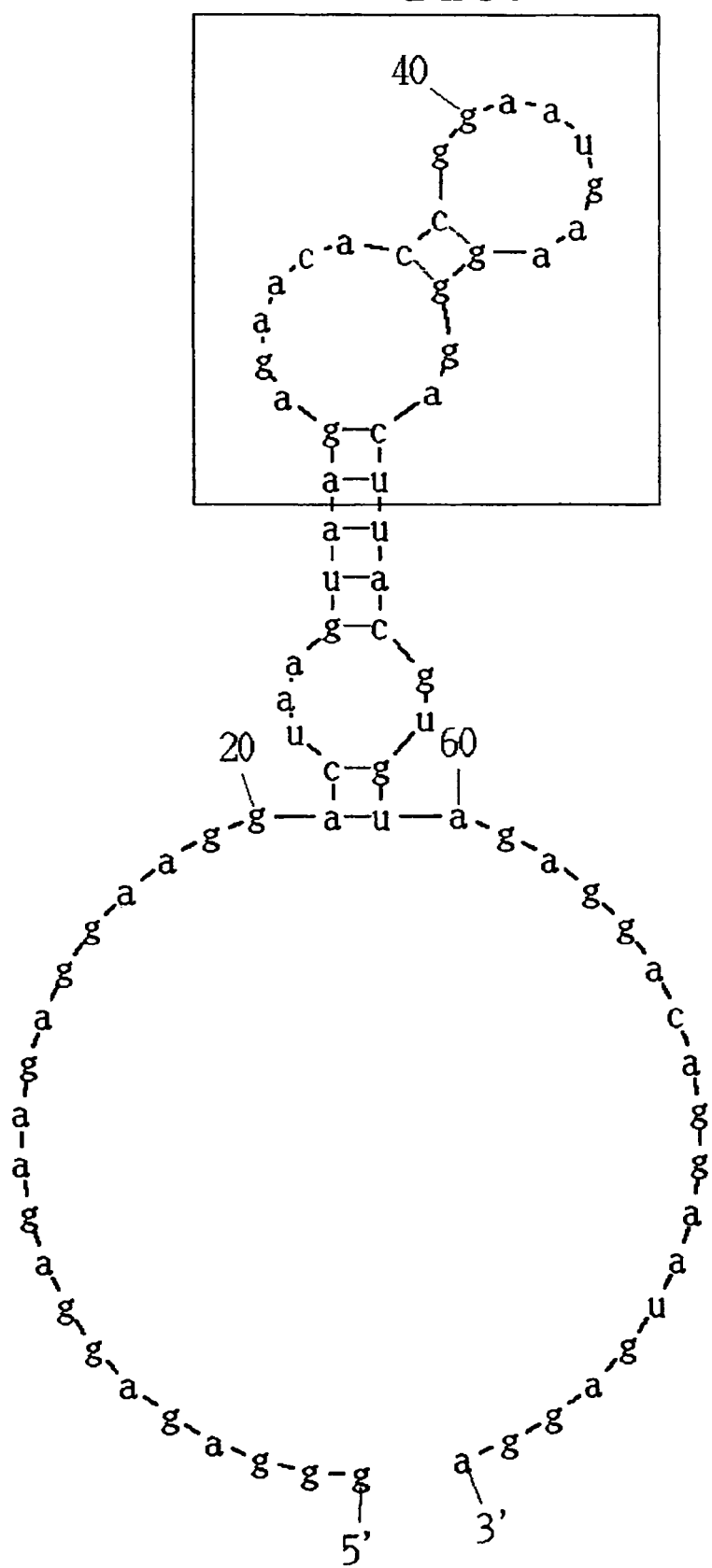
FIG. 2A shows one of the two secondary structures of RNA shown by SEQ ID NO:2 predicted by the MFOLD program, wherein the part enclosed in a square shows a consensus region.
Figure 2B:
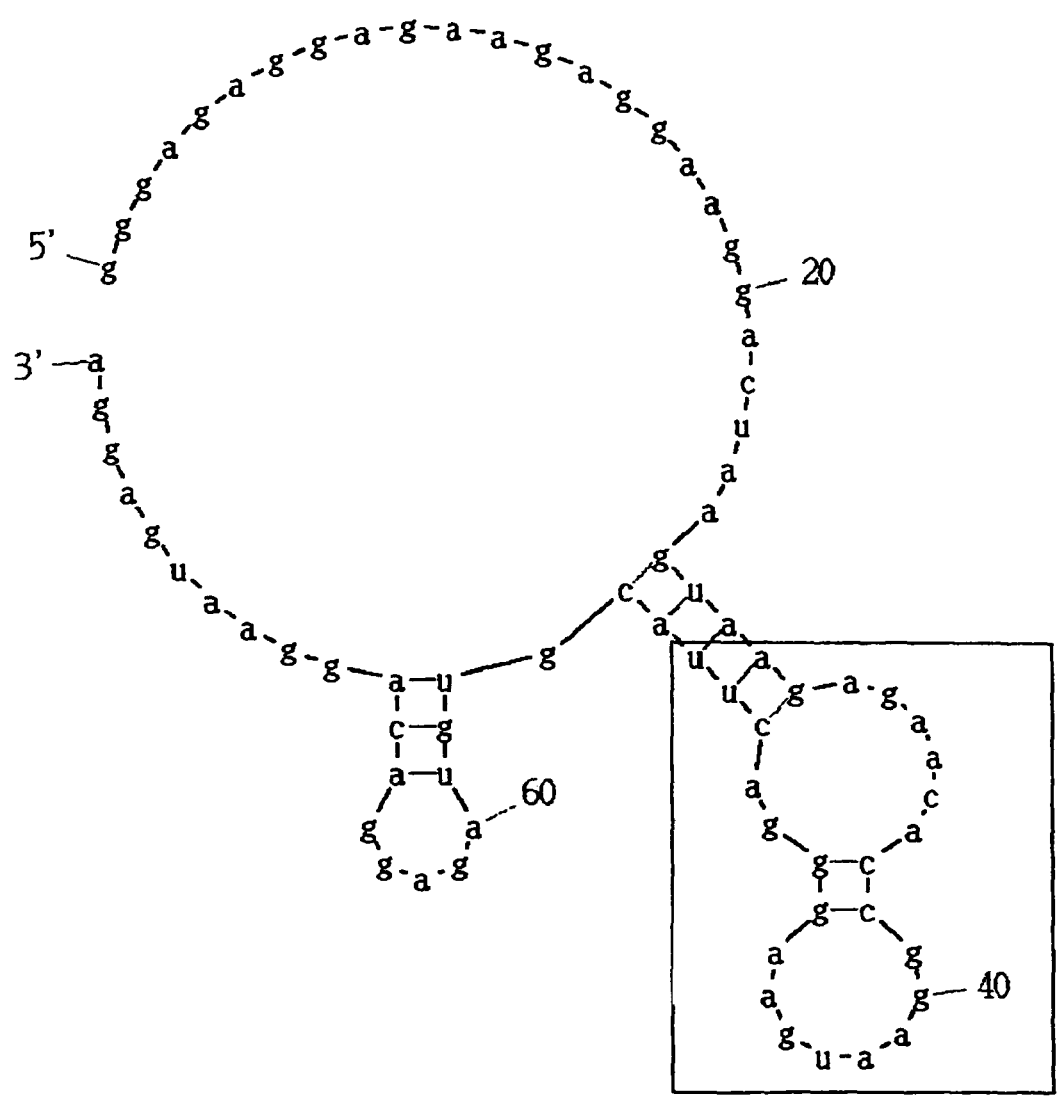
FIG. 2B shows the other secondary structure of RNA shown by SEQ ID NO:2 predicted by the MFOLD program, wherein the part enclosed in a square shows a consensus region.
Figure 3A:
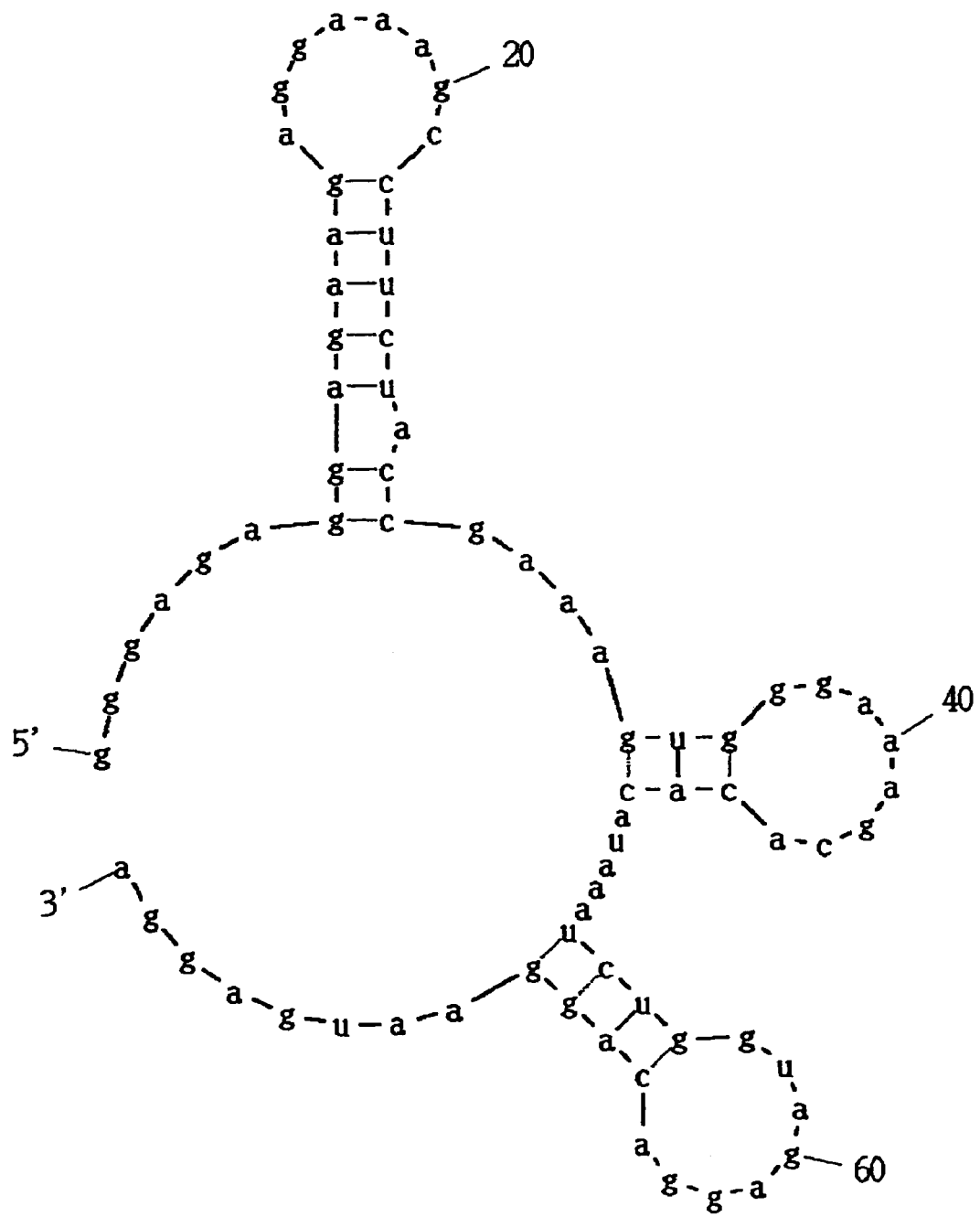
FIG. 3A shows one of the two secondary structures of RNA shown by SEQ ID NO:3 predicted by the MFOLD program.
Figure 3B:
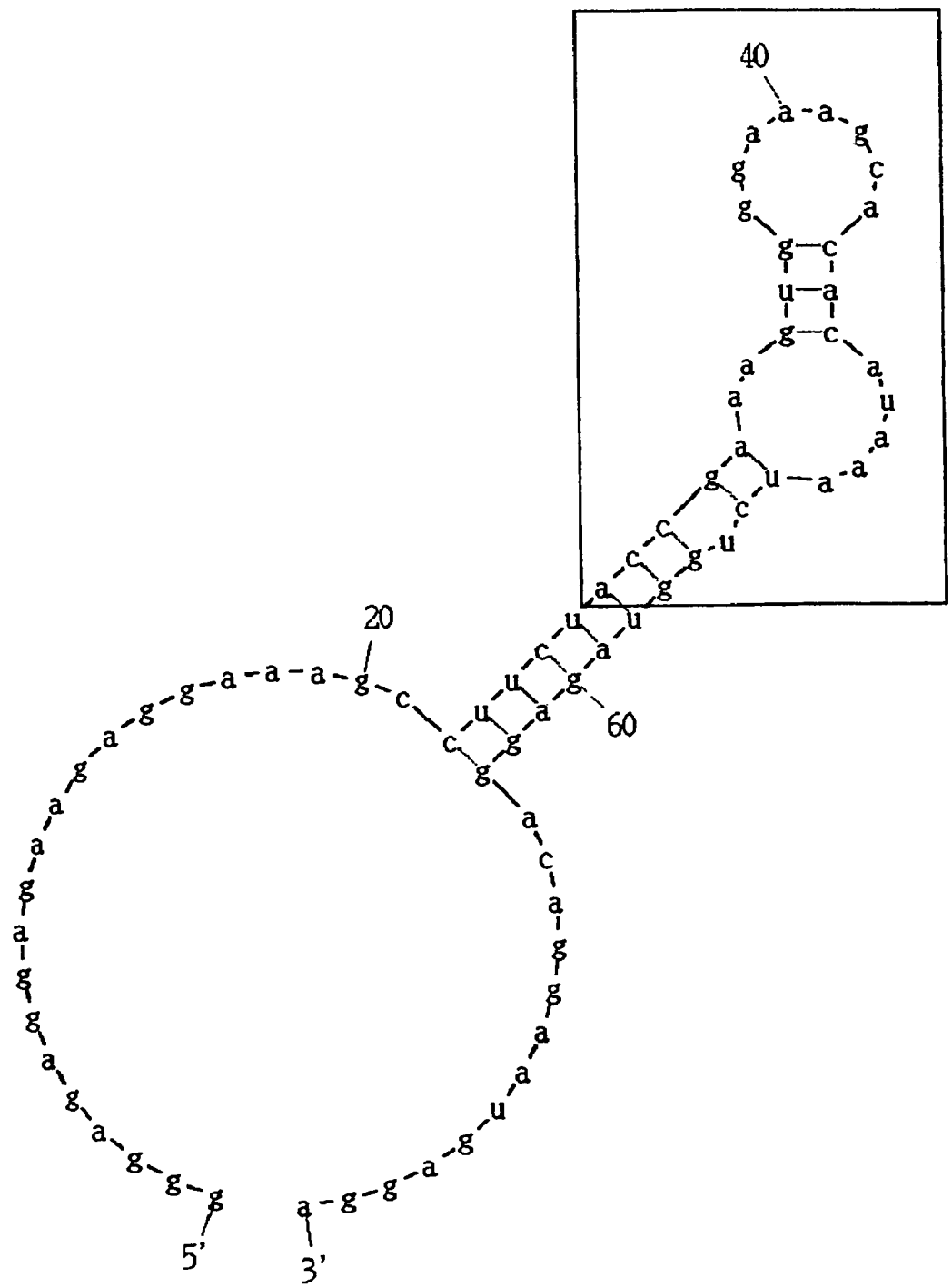
FIG. 3B shows the other secondary structure of RNA shown by SEQ ID NO:3 predicted by the MFOLD program, wherein the part enclosed in a square shows a consensus region.
Figure 4:
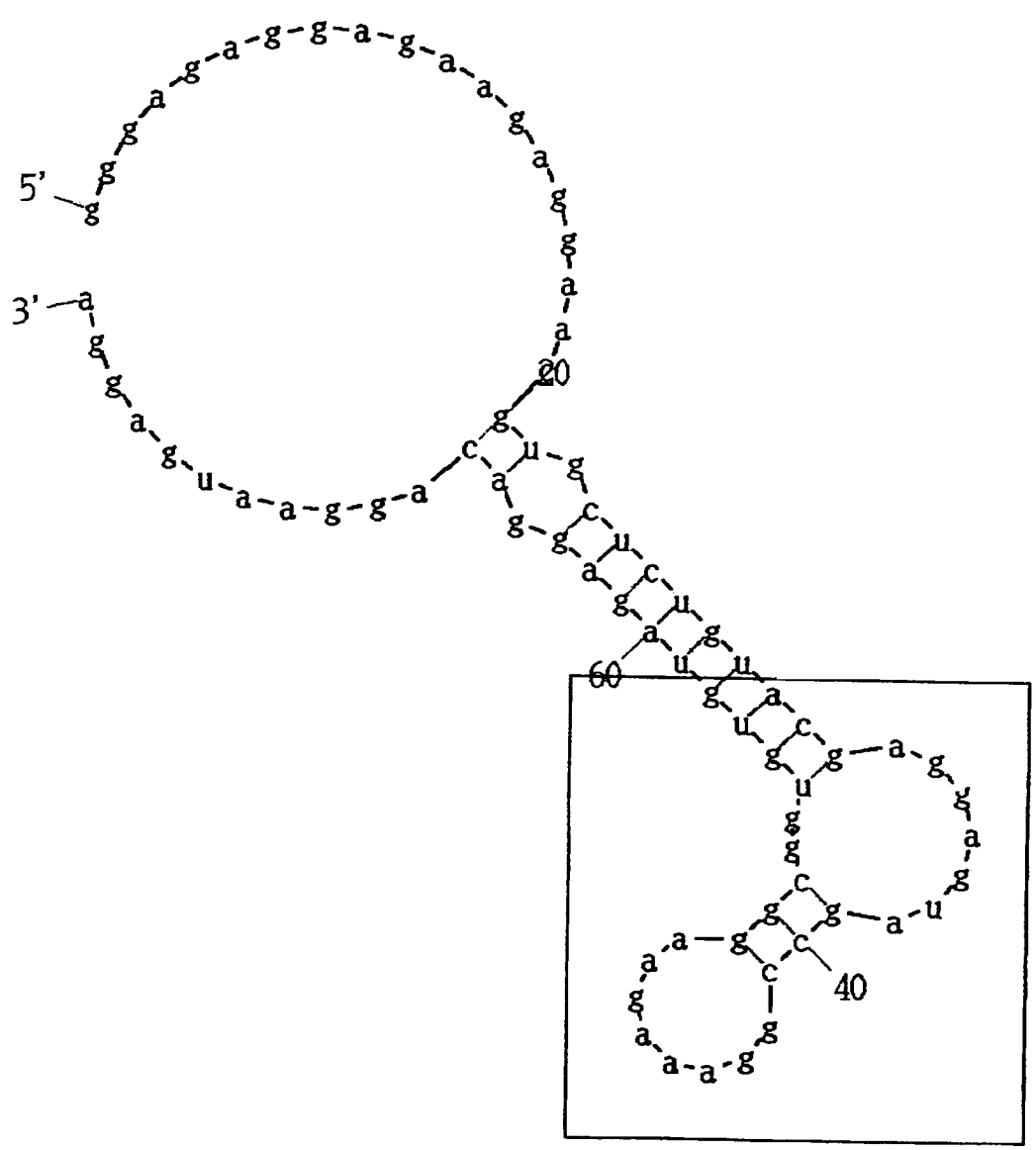
FIG. 4 shows the secondary structure of RNA shown by SEQ ID NO:4 predicted by the MFOLD program, wherein the part enclosed in a square shows a consensus region.
Figure 5:
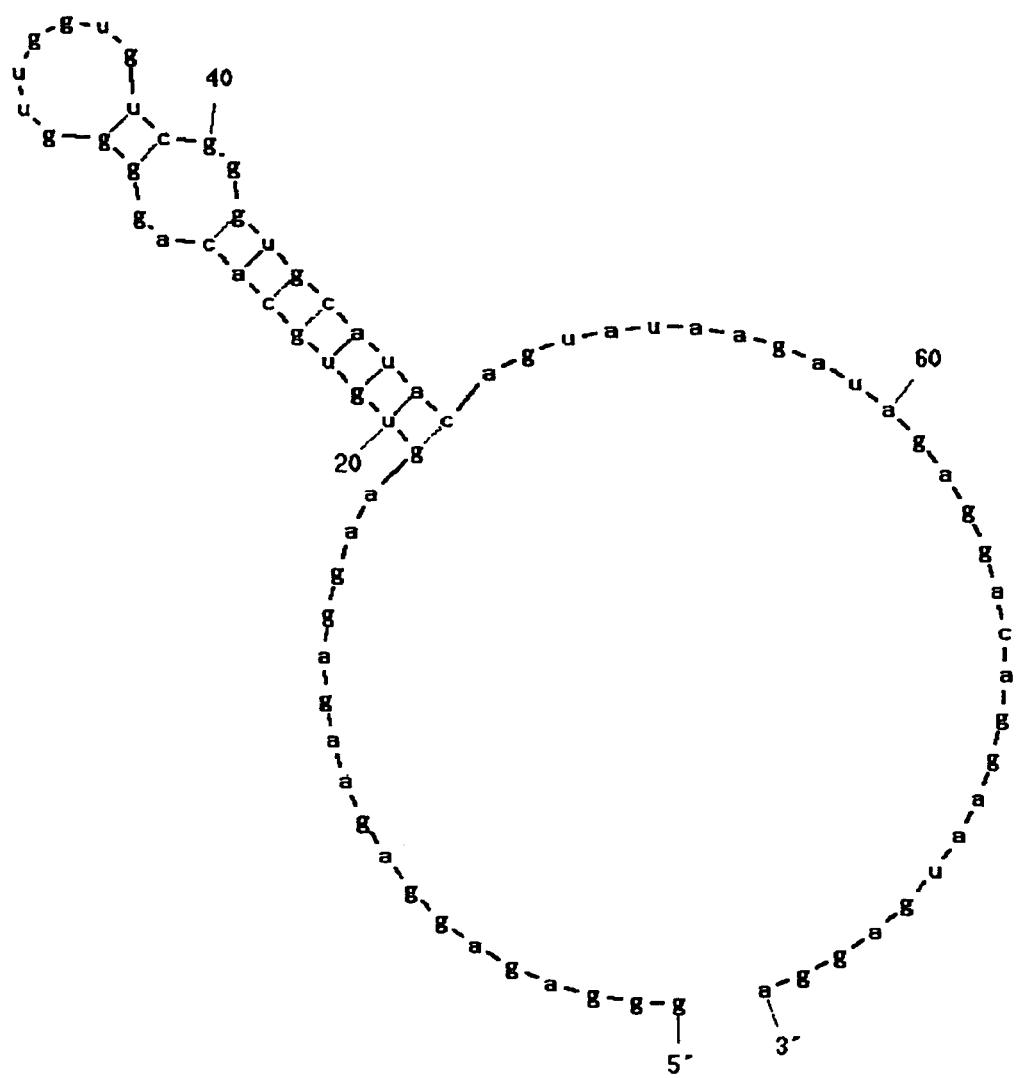
FIG. 5 shows the secondary structure of RNA shown by SEQ ID NO:5 predicted by the MFOLD program.

The present invention provides an aptamer possessing a binding activity for midkine (MK). The aptamers of the present invention are capable of inhibiting activities of MK.

An aptamer refers to a nucleic acid molecule having a binding affinity for a particular target molecule. The aptamer can also inhibit the activity of a particular target molecule by binding to the particular target molecule. The aptamer of the present invention can be an RNA, a DNA, a modified nucleic acid or a mixture thereof. The aptamer of the present invention can also be in a linear or circular form.

An inhibitory activity against MK means inhibition of any biological activities of MK. As examples of the biological activities of MK, migration activities for cells (e.g., macrophages, neutrophils, eosinophils, vascular smooth muscle cells, tumor cells, osteoblasts, nerve cells and progenitor cells thereof) (Takada et al., 1997, J. Biochem. 122, 453-458, Horiba et al., 2000, J. Clin. Invest. 105, 489-495, Maeda et al., 1999, J. Biol. Chem. 274, 12474-12479, Qi et al., 2001, J. Biol. Chem. 276, 15868-15875), proliferation and differentiation promotion activities for cells (e.g., tumor cells, fibroblasts, keratinocytes, nerve cells, chondrocytes and progenitor cells thereof) (Muramatsu and Muramatsu, 1991, Biochem. Biophys. Res. Commun. 177, 652-658, Muramatsu et al., 1993, Dev. Biol. 159, 392-402, Takei et al., 2001, Cancer Res. 61, 8486-8491), inhibitory activities against the proliferation and functions of regulatory T cells, elongation promotion activities for nerve cell neurites, inhibitory activities against apoptosis of cells (e.g., tumor cells, nerve cells), neovascularization induction activities for cells (e.g., tumor cells), synapse formation induction activities for myoblasts, fibrinolytic system promotion activities for vascular endothelial cells, IL-8 production promotion activities for vascular smooth muscle cells and the like can be mentioned.

Therefore, as examples of inhibitory activities against MK, inhibitory activities against these activities can be mentioned. The aptamer of the present invention can possess inhibitory activities against MK derived from any mammals. As examples of such mammals, primates (e.g., humans, monkeys), rodents (e.g., mice, rats, guinea pigs), as well as companion animals, domesticated animals and work animals (e.g., dogs, cats, horses, bovines, goat, sheep, pigs) can be mentioned.

The aptamers of the present invention are not particularly limited, as far as they are capable of binding to an optionally chosen portion of MK to inhibit an activity thereof; for example, by binding to the N-terminal fragment or C-terminal fragment of MK, the aptamers of the present invention are capable of inhibiting activities of MK. The amino acid sequence of human MK is shown by GenBank accession number BC011704, the secretory protein being configured with 121 amino acid residues from lysine 23 to aspartic acid 143. Generally, the lysine residue 23 is denoted by the amino acid residue at position 1. Human MK consists of an N-terminal fragment consisting of amino acid residues 1 to 52, a C-terminal fragment consisting amino acid residues 62 to 121 and a loop region that connects the fragments, but the boundary of the N-terminal fragment and the C-terminal fragment may be any loop portion of MK (53-61), and cannot be defined precisely.

The length of the aptamer of the present invention is not limited, and can usually be about 15 to about 200 nucleotides, and can be, for example, not more than about 100 nucleotides, preferably not more than about 80 nucleotides, more preferably not more than about 60 nucleotides, most preferably not more than about 45 nucleotides. The length of the aptamer of the present invention may be, for example, not less than about 18, 20 or 25 nucleotides. If the total number of nucleotides is smaller, chemical synthesis and mass-production will be easier, and there is a major advantage in terms of cost. It is also thought that chemical modification is easy, stability in the body is high, and toxicity is low.

Each of the nucleotides contained in the aptamer of the present invention, whether identical or different, can be a nucleotide comprising a hydroxyl group at the 2' position of ribose (e.g., ribose of pyrimidine nucleotide) (i.e., an unsubstituted nucleotide) or a nucleotide having the hydroxyl group substituted by an optionally chosen atom or group at the 2' position of ribose. As examples of such an optionally chosen atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned. The aptamer of the present invention can also be one wherein at least one kind (e.g., 1, 2, 3 or 4 kinds) of nucleotide comprises a nucleotide comprising a hydroxyl group, or the above-described optionally chosen atom or group, for example, at least two kinds (e.g., 2, 3 or 4 kinds) of groups selected from the group consisting of a hydrogen atom, a fluorine atom, a hydroxyl group and an —O-Me group, at the 2' position of ribose. In the aptamers of the present invention, all nucleotides can be nucleotides comprising a hydroxyl group, or an optionally chosen atom or group described above, for example, a group selected from the group consisting of a hydrogen atom, a fluorine atom, a hydroxyl group and an —O-Me group, at the 2'-position of ribose.

An example of an aptamer of the present invention can have a potential secondary structure comprising one or more regions selected from the group consisting of single-strand regions (e.g., gggagaggaac), first stem regions (e.g., gacg and complementary chains thereof), internal loop regions (e.g., aggagua and gg), second stem regions (e.g., gcc and complementary chains thereof), and internal loop regions (e.g., ggaaagaa). Another example of an aptamer of the present invention can have a potential secondary structure comprising one or more regions selected from the group consisting of single-strand regions (e.g., gggaaggaggaa), first stem regions (e.g., gugcac and complementary chains thereof), internal loop regions (e.g., ag and gg), second stem regions (e.g., gg and complementary chains thereof), and internal loop regions (e.g., guuggug).

As used herein, "potential secondary structure" refers to a secondary structure capable of occur stably under physiological conditions; for example, whether or not a potential secondary structure is present can be determined using the structure prediction programs described in Examples. A stem region refers to a portion where a double strand is formed by a base pair in two or more continuous nucleotides (e.g., G-C, A-U, A-T). An internal loop portion refers to a non stem region formed between two different stem regions. A hairpin loop region refers to a partial structure formed by one stem region, being a loop region formed on the opposite side to the 5' end and 3' end of an aptamer chain. A single-strand region refers to a terminal portion of a polynucleotide chain, being a region that does not correspond to the above-described stem region, internal loop region or hairpin loop region.

The aptamers of the present invention can also have the capability of binding to the N-terminal fragment and/or C-terminal fragment of MK. The aptamer shown by SEQ ID NO:39 and altered forms thereof, like heparin and chondroitin sulfate E, exhibit high binding activity for the C-terminal fragment. Heparin is thought to bind to the C-terminal fragment at the cluster I and cluster II regions. Chondroitin sulfate E is thought to bind to the C-terminal fragment at the cluster I region. MK is known to interact with PTPζ, which comprises chondroitin sulfate as a constituent molecule thereof. PTPζ is expressed in fetal nerve cells and osteoblast-like cells, and in the presence of MK, the migration of these cells is promoted. In the present invention, an aptamer capable of binding to the C-terminal fragment to inhibit cell migration, and an aptamer that binds mainly to the N-terminal fragment to inhibit cell migration are provided.

The aptamers of the present invention are also capable of inhibiting activities of MK (e.g., cell migration activity of MK), and can have the feature of being unable to inhibit an activity of PTN (e.g., cell migration activity of PTN). PTN is the only family protein of MK having a homology of 50%, they have very similar three-dimensional structures, and the amino acid residues important to the binding with chondroitin sulfate and heparin are conserved.

The aptamer of the present invention can also be (a) an aptamer comprising a nucleotide sequence selected from one of SEQ ID NO:1 to 70 (but the uracil may be thymine), (b) an aptamer comprising a nucleotide sequence selected from one of SEQ ID NO:1 to 70 (but the uracil may be thymine) having one or more nucleotides substituted, deleted, inserted or added, or (c) a conjugate selected from the group consisting of a conjugate of a plurality of units of (a) above, a conjugate of a plurality of units of (b) above, and a conjugate of a plurality of units of (a) and (b) above. In (b) above, the number of nucleotides substituted, deleted, inserted or added is not particularly limited, as long as it is several, and the number of nucleotides can be, for example, not more than about 30, preferably not more than about 20, more preferably not more than about 10, still more preferably not more than 5, most preferably 4, 3, 2 or 1. In (c) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)n- linker, —(CH$_2$CH$_2$O)n- linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plurality of conjugates is not particularly limited, as long as it is two or more, and the plurality can be, for example, 2, 3 or 4. Each of the nucleotides in (a) to (c) above, whether identical or different, can be a nucleotide comprising a hydroxyl group at the 2' position of ribose or a nucleotide having the hydroxyl group substituted by an optionally chosen group (e.g., hydrogen atom, fluorine atom or —O-Me group) at the 2' position of ribose (e.g., ribose of pyrimidine nucleotide).

Figure 9:
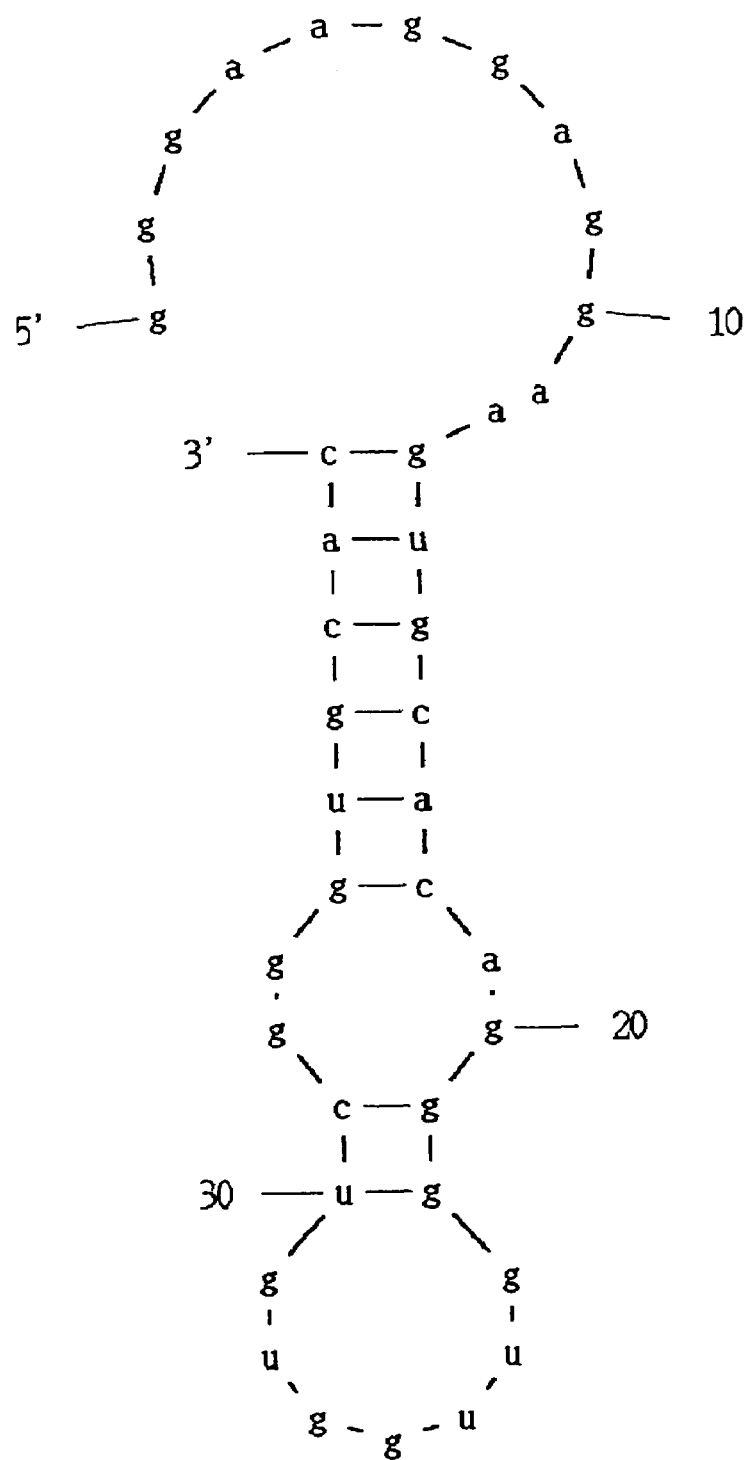
FIG. 9 shows the secondary structure of RNA shown by SEQ ID NO:61 predicted by the MFOLD program.

In a particular aspect, the aptamers of the present invention are classifiable roughly into three kinds according to the structures thereof. A first aptamer is an aptamer consisting of the nucleotide sequence shown by SEQ ID NO:61 or a mutant thereof. An aptamer consisting of the nucleotide sequence shown by SEQ ID NO:61, when the secondary structure thereof is predicted by the MFOLD program, has the potential secondary structure shown in FIG. 9, being configured with a single-strand region, a first stem region, an internal loop region, a second stem region, and a hairpin loop region. In this aptamer, substitution, deletion, insertion and/or addition of several nucleotides are acceptable in the single-strand region, firststem region, internal loop region, second stem region, and hairpin loop region. For example, in this aptamer, insertion of several nucleotides into the single-strand region, insertion of several nucleotides into the first stem region, and addition of several nucleotides to the 3' end single-strand region (e.g., SEQ ID NO:5) are acceptable. Such an aptamer binds more strongly to the N-terminal fragment than to the C-terminal fragment of MK.

A second aptamer is an aptamer consisting of the nucleotide sequence shown by SEQ ID NO:20 or a mutant thereof.

Figure 8:
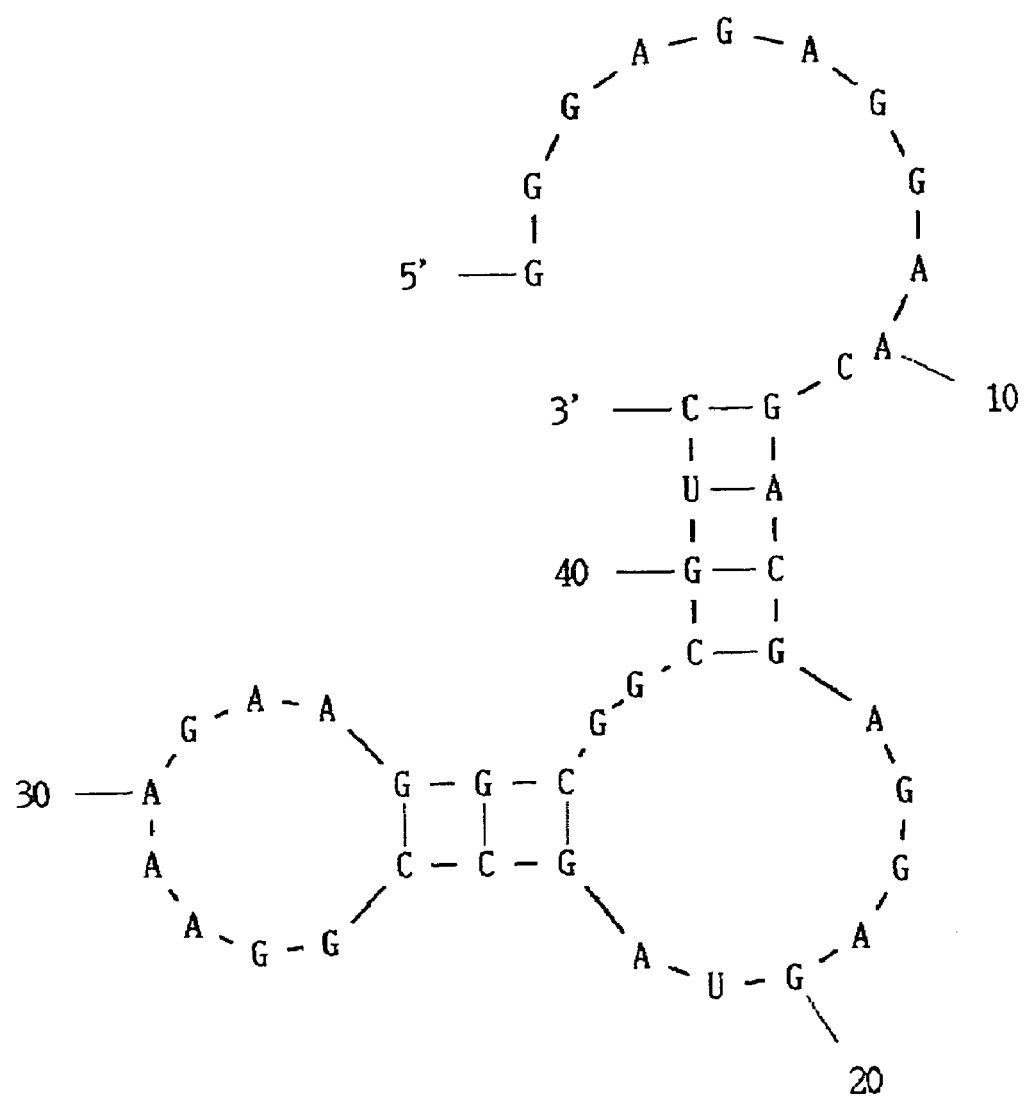
FIG. 8 shows the secondary structure of RNA shown by SEQ ID NO:20 predicted by the MFOLD program.

An aptamer consisting of the nucleotide sequence shown by SEQ ID NO:20, the secondary structure predicted by the MFOLD program has the potential secondary structure shown in FIG. 8, being configured with a single-strand region, a first stem region, an internal loop region, a second stem region, and a hairpin loop region. In this aptamer, substitution, deletion, insertion and/or addition of several nucleotides are acceptable in the single-strand region, first stem region, internal loop region, second stem region, and hairpin loop region. For example, in this aptamer, addition of several nucleotides to the single-strand region, the first stem region and/or the 3' end (e.g., SEQ ID NO:4) is acceptable. Such an aptamer exhibits almost no affinity for the N-terminal fragment of MK, and binds strongly to the C-terminal fragment.

A third aptamer can be an aptamer consisting of the nucleotide sequence shown by SEQ ID NO:1 or a mutant thereof.

The aptamer of the present invention may be one wherein a sugar residue (e.g., ribose) of each nucleotide has been modified to increase the MK binding activity, stability, drug deliverability and the like. As examples of the site to be modified in a sugar residue, one having the oxygen atom at the 2'-position, 3'-position and/or 4'-position of the sugar residue replaced with another atom, and the like can be mentioned. As examples of the modification, fluoration, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see, for example, Sproat et al., (1991) Nucle. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the MK binding activity and the like. As examples of such alterations, 5-position pyrimidine alteration, 6- and/or 8-position purine alteration, alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the P(O)O group may be substituted with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)].

The joining group is, for example, —O—, —N— or —S—, and nucleotides can bind to an adjoining nucleotide via these joining groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamers of the present invention can be chemically synthesized by disclosures herein and a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking bonds based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall steric structure does not change widely.

An aptamer can be prepared by utilizing the SELEX method or an improved version thereof (for example, Ellington et al., (1990) Nature, 346, 818-822; Tuerk et al., (1990) Science, 249, 505-510). In the SELEX method, by increasing the number of rounds or using a competing substance, an aptamer exhibiting a stronger binding force for the target substance is concentrated and selected. Hence, by adjusting the number of rounds of SELEX, and/or changing the competitive condition, aptamers with different binding forces, aptamers with different binding modes, and aptamers with the same binding force and binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, and this does not mean the binding thereof to the active site of the target substance. Therefore, the aptamers obtained by SELEX do not always act on a function of the target substance. MK has a lysine-rich region in the tail region of each of the N end and C end thereof, to which a nucleic acid is thought to bind non-specifically. This tail portion is not considered to be important in the binding of heparin or chondroitin sulfate. It is not easy to prepare an aptamer that effectively inhibits an activity of MK in such an environment. In fact, in the present invention, the cell migration inhibitory activities of 23 kinds of aptamers were examined, and only 4 kinds of aptamers retained not less than 50% of activity.

The thus-selected aptamers with activity can be made to have even higher performance by performing optimized SELEX. Optimized SELEX refers to a method in which SELEX is performed again after preparing a template wherein an aptamer with a certain fixed sequence is partially changed to include random sequences or a template doped with about 10 to 30% of random sequences.

An aptamer obtained by SELEX has a length of about 80 nucleotides, and this is difficult to prepare as a pharmaceutical as it is. Hence, it is necessary to repeat try-and-error efforts to shorten the aptamer to a length of about 50 nucleotides or less enabling easy chemical synthesis.

Depending on the primer design for an aptamer obtained by SELEX, the ease of the subsequent minimization operation changes. Unless the primer is designed successfully, subsequent development will be impossible even if an aptamer with activity is selected by SELEX.

Aptamers are easily alterable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. An aptamer with the predicted new sequence can easily be chemically synthesized, and it can be determined whether or not the aptamer retains the activity using an existing assay system.

If a region important to the binding of the aptamer obtained with the target substance is identified by repeated try-and-error efforts as described above, the activity remains unchanged in many cases even when a new sequence is added to both ends of the sequence. The length of the new sequence is not particularly limited.

Modifications, like sequences, afford a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule or a plurality of kinds of nucleic acid molecules (e.g., a library of nucleic acid molecules with different numbers for "a" or "b") consisting of a nucleotide sequence shown by the formula:

| Primer sequence (i) | -(N)a-fixed sequence-(N)b- | Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be an optionally chosen number, and can be, for example, 1 to about 100, preferably 1 to about 50, more preferably 1 to about 30, still more preferably 1 to about 20 or 1 to about 10], and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metal protease (MMP), and Factor X, polynucleotides that can be cleaved by nucleases or restriction endonuclease.

The aptamer or the complex of the present invention can be used as, for example, a pharmaceutical or a reagent (e.g., diagnostic reagents, test reagents (including experimental reagents)). For example, the aptamers or the complex of the present invention can be used as inhibitors of cell migration, promoters of regulatory T cell proliferation, promoters of regulatory T cell suppressive function, apoptosis inhibition suppressants, cell proliferation inhibitors, cell differentiation inhibitors, drug delivery agents, probes for in vivo imaging, probes for measuring blood concentrations of MK, probes for tissue staining, probes for ELISA, and ligands for MK separation and purification.

The aptamers or the complex of the present invention can also be used in the prevention or treatment of various diseases such as autoimmune diseases (e.g., multiple sclerosis, systemic lupus erythematosus (SLE), Sjögren's disease, polymyositis (PM), dermatomyositis (DM), rheumatic arthritis (rheumatoid arthritis (RA), osteoarthritis (OA)), inflammatory enteritis (Crohn's disease and the like), progressive systemic sclerosis (PSS), periarteritis nodosa (PN), thyroid diseases (Basedow's disease and the like), Guillain-Barré syndrome, primary biliary cirrhosis (PBC), idiopathic thrombocytopenic purpura, autoimmune hemolytic anemia, myasthenia gravis (MG), amyotrophic lateral sclerosis (ALS), type I diabetes, psoriasis, asthma, neutrophil functional abnormalities), cancers (e.g., esophageal cancer, thyroid cancer, urinary bladder cancer, colorectal cancer, gastric cancer, pancreatic cancer, chest cancer, liver cancer, lung cancer, breast cancer, neuroblastoma, glioblastoma, uterine cancer, ovarian cancer, Wilms' tumor, prostatic cancer), postoperative adhesion, endometriosis, rejections in transplantation, allergies, restenosis following vascular reconstruction surgery, cardiac coronary arterial vascular obstructive disease, cerebral vascular obstructive disease, renal vascular obstructive disease, peripheral vascular obstructive disease, arteriosclerosis, and cerebral infarction. In particular, the aptamers of the present invention inhibit the cell migration activity of MK, and are therefore useful in preventing or treating multiple sclerosis, postoperative adhesion, endometriosis, rheumatoid arthritis, and vascular stenosis.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a liquid preparation prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The pharmaceutical of the present invention can be coated by a method known per se for the purpose of taste masking, enteric dissolution, sustained release and the like as required. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., red iron oxide, titanium dioxide and the like) and the like are used. The pharmaceutical may be a rapid-release preparation or sustained-release preparation. As examples of sustained-release base materials, liposome, atherocollagen, gelatin, hydroxyapatite, PLGA and the like can be mentioned.

As preparations suitable for parenteral administration (for example, intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. Furthermore, in addition to injectable liquids, inhalants and ointments are also possible. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethyleneglycol dioleate, tetrahydroflufuryl oleate, ethyl oleate, isopropyl myristate, glyceryl trioleate, glyceryl monolaurate, glyceryl monoleate, glyceryl monostearate, glyceryl monolysinoate, cetyl alcohol, stearyl alcohol, polyethyleneglycol 400, cetylpyridinium chloride, sorbitan trioleate (trade name Span 85), sorbitan monoleate (trade name Span 80), sorbitan monolaurate (trade name Span 20), polyoxyethylene hardened castor oil (trade name HCO-60), polyoxyethylene (20) sorbitan monolaurate (trade name Tween 20), polyoxyethylene (20) sorbitan monoleate (trade name Tween 80), lecithin of natural resource origin (trade name EPICLON), oleylpolyoxyethylene (2) ether (trade name Brij 92), stearyl polyoxyethylene (2) ether (trade name Brij 72), lauryl polyoxyethylene (4) ether (trade name Brij 30), oleylpolyoxyethylene (2) ether (trade name Genapol 0-020), block copolymer of oxyethylene and oxypropylene (trade name Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient and used as a preparation.

An inhalant can be produced according to a conventional method. Specifically, an inhalant can be produced by powdering or liquefying the above-described aptamer or complex of the present invention, blending it in an inhalation propellant and/or carrier, and filling it in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as gaseous nitrogen and gaseous carbon dioxide and the like can be mentioned.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and/or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying MK.

The aptamer and/or the complex of the present invention can be immobilized onto a solid phase carrier by a method known per se. For example, a method that introduces an affinity substance (e.g., those described above) or a predetermined functional group into the aptamer and/or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating MK. The method of purification and concentration of the present invention can comprise adsorbing MK to the solid phase carrier of the present invention, and eluting the adsorbed MK with an eluent. Adsorption of MK to the solid phase carrier of the present invention can be achieved by a method known per se. For example, an MK-containing sample (e.g., bacterial or cell culture or culture supernatant, blood) is introduced into the solid phase carrier of the present invention or a composition containing the same. MK elution can be achieved using an eluent such as a neutral solution. The neutral eluent is not particularly limited, and can have a pH of, for example, about 6 to about 9, preferably about 6.5 to about 8.5, and more preferably about 7 to about 8. The neutral solution can also be one comprising, for example, a potassium salt (e.g., NaCl, KCl), a magnesium salt (e.g., $MgCl_2$), a surfactant (e.g., Tween 20, Triton, NP40), or glycerin. The method of purification and concentration of the present invention can further comprise washing the solid phase carrier using a washing solution after MK adsorption. As examples of the washing solution, those containing urea, a chelating agent (e.g., EDTA), Tris, an acid, or an alkali, and the like can be mentioned. The method of purification and concentration of the present invention can still further comprise heating the solid phase carrier. This step enables the regeneration and sterilization of the solid phase carrier.

The present invention also provides a method of detecting and quantifying MK. The method of detection and quantitation of the present invention can comprise measuring MK by utilizing the aptamer of the present invention (e.g., by the use of the complex and solid phase carrier of the present invention). The method of detecting and quantifying MK can be performed in the same manner as an immunological method, except that the aptamer of the present invention is used in place of an antibody. Therefore, by using the aptamer of the present invention in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique (e.g., use as a substitute for secondary antibody in Western blot technique), immunohistochemical staining method, and cell sorting method, detection and quantitation can be performed. These methods can be useful in, for example, measuring MK contents in a living organism or biological sample, and diagnosing MK-related diseases.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLE 1

Preparation of Nucleic Acids that Bind Specifically to Midkine 1

Nucleic acids that bind specifically to midkine were prepared using the SELEX method. SELEX was performed with improvements of the method of Ellington et al. (Ellington and Szostak, Nature 346, 818-822, 1990) and the method of Tuerk et al. (Tuerk and Gold, Science 249, 505-510, 1990). As the target substance, human midkine was prepared using yeast with reference to a method of Murasugi et al. (Murasugi and Tohma-Aiba, Protein Expression and Purification 27, 244-252, 2003). Hereinafter, unless otherwise specified, midkine means human midkine. Midkine was immobilized on an agarose resin (NHS-activated Sepharose, manufactured by Amersham Bioscience) by aminocoupling. The aminocoupling was performed as directed in the specifications of Amersham Bioscience. The amount immobilized was confirmed by examining the midkine solution just before immobilization and the supernatant just after immobilization by SDS-PAGE. As a result of the SDS-PAGE, no band of midkine was detected in the supernatant; it was confirmed that nearly all of the midkine used had been coupled. This means that about 175 μg of midkine was immobilized to about 70 μL of the resin.

The RNA used in the first round (40N-RNA) was obtained by transcribing a chemically synthesized DNA using the DuraScribe™ T7 Transcription Kit (manufactured by Epicentre). The RNA obtained by this method has the 2'-position of the ribose of the pyrimidine nucleotide fluoro-substituted. The DNA 94 nucleotides long shown below, having a primer sequence at each end of a 40-nucleotide random sequence was used as DNA template. The DNA template and the primers were prepared by chemical synthesis (manufactured by Operon).

```
DNA template:
                                        (SEQ ID NO: 71)
5'-tcctcattcctgtcctcta-40N-ttcctcttctcctctccc-3'

Primer Fwd:
                                        (SEQ ID NO: 72)
5'-taatacgactcactatagggagaggagaagaggaa-3'

Primer Rev:
                                        (SEQ ID NO: 73)
5'-tcctcattcctgtcctcta-3'
```

N represents any one of A, G, C and T. The primer Fwd comprises a promoter sequence of T7 RNA polymerase. The variation of the RNA pool used in the first round was theoretically $10^{14}$.

The RNA pool was added to the midkine-immobilized resin, and allowed to stand at room temperature for 30 minutes. After 30 minutes, to remove the RNA not bound to midkine, the resin was washed with solution A. Here, the solution A was a mixed solution of 145 mM sodium chloride, 5.4 mM potassium chloride, 1.8 mM calcium chloride, 0.8 mM magnesium chloride, and 20 mM Tris (pH7.6). The midkine-bound RNA was recovered via heating at 95° C. for 10 minutes with the addition of an eluent. As the eluent, a mixed solution of 7 M urea, 3 mM EDTA, and 100 mM TRIS, adjusted to pH 6.6, was used. The recovered RNA was amplified by RT-PCR and transcribed using the DuraScribe™ T7 Transcription Kit, and this was used as the pool for the next round. With this procedure taken as 1 round, the same operation was performed in 7 rounds. After completion of SELEX, the PCR product was cloned into pGEM-T Easy vector (manufactured by Promega), and the *Escherichia coli* strain DH5α (manufactured by Toyobo) was transformed therewith. After the plasmid was extracted from a single colony, the base sequences of 48 clones were determined using a DNA sequencer (ABI PRISM 3100, manufactured by ABI).

After SELEX was performed in 7 rounds, the sequences were examined; the sequences exhibited convergence. Twenty copies of the sequence shown by SEQ ID NO:1 existed, and one copy of the 2-base substituted form existed. Two copies of the sequence shown by SEQ ID NO:2 existed. One copy of each of the sequences shown by SEQ ID NO:3 to 5 existed. The secondary structures of the RNAs shown by SEQ ID NO:1 to 5 were estimated using the MFOLD program (M. Zuker, Nucleic Acids Res. 31 (13), 3406-3415, 2003). As a result, internal loop-stem-hairpin loop structures morphologically similar to the RNAs shown by SEQ ID NO:2, 3, and 4 were seen (FIG. 1 to 5). All hairpin loops were made up of eight nucleotides; 2 and 3 were 1-base substituted forms compared with SEQ ID NO:4. Regarding the stems, SEQ ID NO:2 was configured with two base pairs, and SEQ ID NO:3 and 4 were configured with three base pairs.

Each nucleotide sequence is shown in the following. The parentheses in each nucleotide show modifications at the 2'-position and F is fluorine atom (hereinafter the same).

SEQ ID NO: 1:
gggagaggagaagaggaaau(F)agu(F)u(F)aagggu(F)gaau(F)u (F)u(F)gc(F)gaaagc(F)u(F)au(F)u(F)u(F)u(F)agu(F)c (F)gc(F)agu(F)agaggac(F)aggaau(F)gagga SEQ ID NO: 2:
gggagaggagaagaggaaggac(F)u(F)aagu(F)aagagaac(F)ac (F)c(F)ggaau(F)gaagggac(F)u(F)u(F)ac(F)gu(F)gu(F)a gaggac(F)aggaau(F)gagga SEQ ID NO: 3:
gggagaggagaagaggaaagc(F)c(F)u(F)u(F)c(F)u(F)ac(F)c (F)gaaagu(F)gggaaagc(F)ac(F)ac(F)au(F)aaau(F)c(F)u (F)ggu(F)agaggac(F)aggaau(F)gaga SEQ ID NO: 4:
gggagaggagaagaggaac(F)gu(F)gc(F)u(F)c(F)u(F)gu(F)a c(F)gaggagu(F)agc(F)c(F)ggaaagaaggc(F)ggu(F)gu(F)g u(F)agaggac(F)aggaau(F)gaga SEQ ID NO: 5:
gggagaggagaagaggaagu(F)gu(F)gc(F)ac(F)aggggu(F)u (F)ggu(F)gu(F)c(F)gggu(F)gc(F)au(F)ac(F)agu(F)au (F)aagau(F)agaggac(F)aggaau(F)gaga Sequence of Hairpin Loop

```
SEQ ID NO: 2        -ggaaugaa-
SEQ ID NO: 3        -ggaaagca-
SEQ ID NO: 4        -ggaaagaa-
```

EXAMPLE 2

Preparation of Nucleic Acids that Bind Specifically to Midkine 2

To prepare aptamers that bind to midkine but do not bind to pleiotrophin, a midkine family protein, SELEX including pre-subtraction using pleiotrophin was performed. First, as with midkine, pleiotrophin was immobilized to agarose resin by aminocoupling. Next, the RNA pool was added to the pleiotrophin-bound resin, and allowed to stand at room temperature for 30 minutes. Thereafter, only the supernatant was recovered. Theoretically, this supernatant should not contain an RNA that binds to pleiotrophin. This supernatant was added to the midkine-bound resin, and SELEX was performed in the same manner as Example 1. The pleiotrophin used had been expressed in yeast by the method of Murasugi et al. (Murasugi, Kido, Kumai, and Asami, Biosci. Biotech. Biochem. 67 (10), 2288-2290, 2003). The DNA template and primers used were the same as those used in Example 1.

After completion of 7 rounds, the sequences of 48 clones were checked; convergence was observed in the sequences. Among them, ten copies of the same sequence as SEQ ID NO:3 obtained in Example 1 existed, and one copy of the 1-base substituted form existed. Six copies of the same sequence as SEQ ID NO:2 existed, and two copies of the 1-base substituted form existed. Furthermore, one copy of the same sequence as SEQ ID NO:5 existed.

EXAMPLE 3

Preparation of Nucleic Acids that Bind Specifically to Midkine 3

When midkine is immobilized by aminocoupling, important portions may collapse depending on the site of aminocoupling. Hence, filter binding SELEX using a nitrocellulose membrane, which does not involve immobilization to a carrier, was performed. This is intended to separate nucleic acids that bind to the target protein and nucleic acids that do not bind, on the basis of the fact that proteins are likely to bind to nitrocellulose membranes, whereas nucleic acids are unlikely to bind. An RNA pool and midkine were mixed, allowed to stand for 30 minutes at room temperature, and then the mixture was filtered using a nitrocellulose membrane. After the nitrocellulose membrane was thoroughly washed with solution A, the nitrocellulose membrane was immersed in eluent B and heated at 90° C. for 5 minutes. Subsequently, in the same manner as Example 1, the RNA was recovered by ethanol precipitation, amplified by RT-PCR, and transcribed to the RNA pool for the next round. The DNA template and primers used were the same as those used in Example 1. The eluent B is a mixed liquid of 50% phenol and 6 M urea.

After completion of six rounds, the sequences of 48 clones were checked; no sufficient convergence was obtained. Hence, SELEX was performed in three more rounds; after completion of the nine rounds, the sequences of the 48 clones were checked; sufficient convergence was observed. Among the sequences, 21 copies of the same sequence as SEQ ID NO:2 existed, and four copies of the 1-base substituted form existed. Ten copies of the same sequence as SEQ ID NO:4 existed. Three new sequences were discovered, none of which exhibited convergence.

EXAMPLE 4

Evaluation of Binding Activities by Surface Plasmon Resonance Method

Figure 6:
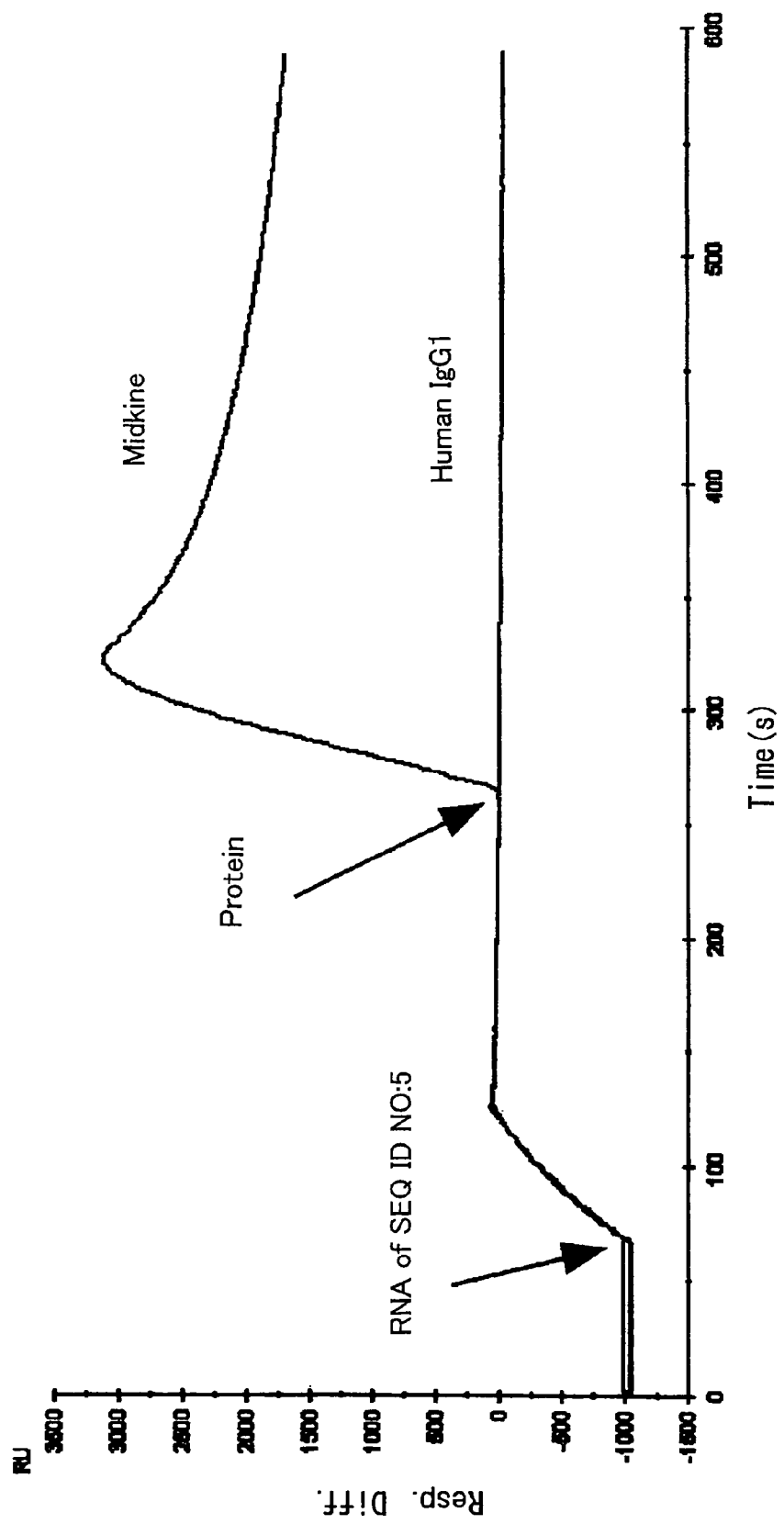
FIG. 6 shows interactions between RNA shown by SEQ ID NO:5 and midkine, and between the RNA and human IgG1 (sensorgram obtained using BIAcore 2000).

The binding activities of the RNAs shown by SEQ ID NO:1 to 5 for midkine were examined by a surface plasmon resonance method. The measurements were performed using BIAcore2000, manufactured by BIAcore. The sensor chip used was the SA chip, which had streptavidin immobilized thereon. Bound thereto was about 1000 RU of a 16-nucleotide Poly dT with biotin bound to the 5' end thereof. The RNA being the ligand had a 16-nucleotide Poly A added to the 3' end thereof, and immobilized to the SA chip via a bond between dT and A. The amount immobilized was about 1000 RU. 70 µL of midkine for analyte, prepared at 0.5 µM, was injected. The running buffer used for BIAcore was solution A. As a result of the measurements, it was found that all of the RNAs shown by SEQ ID NO:1 to 5 bound to midkine (FIG. 6). For negative control, a similar measurement was performed with the 40N-RNA, which comprised a 40-nucleotide random sequence, immobilized. As a result, it was found that the 40N-RNA also possessed affinity for midkine. The degree was high at similar levels to the affinities of the RNAs shown by SEQ ID NO:1 to 5. Because midkine contains large amounts of basic amino acids such as lysine, it is expected to bind nonspecifically to negatively charged nucleic acids.

Figure 7:
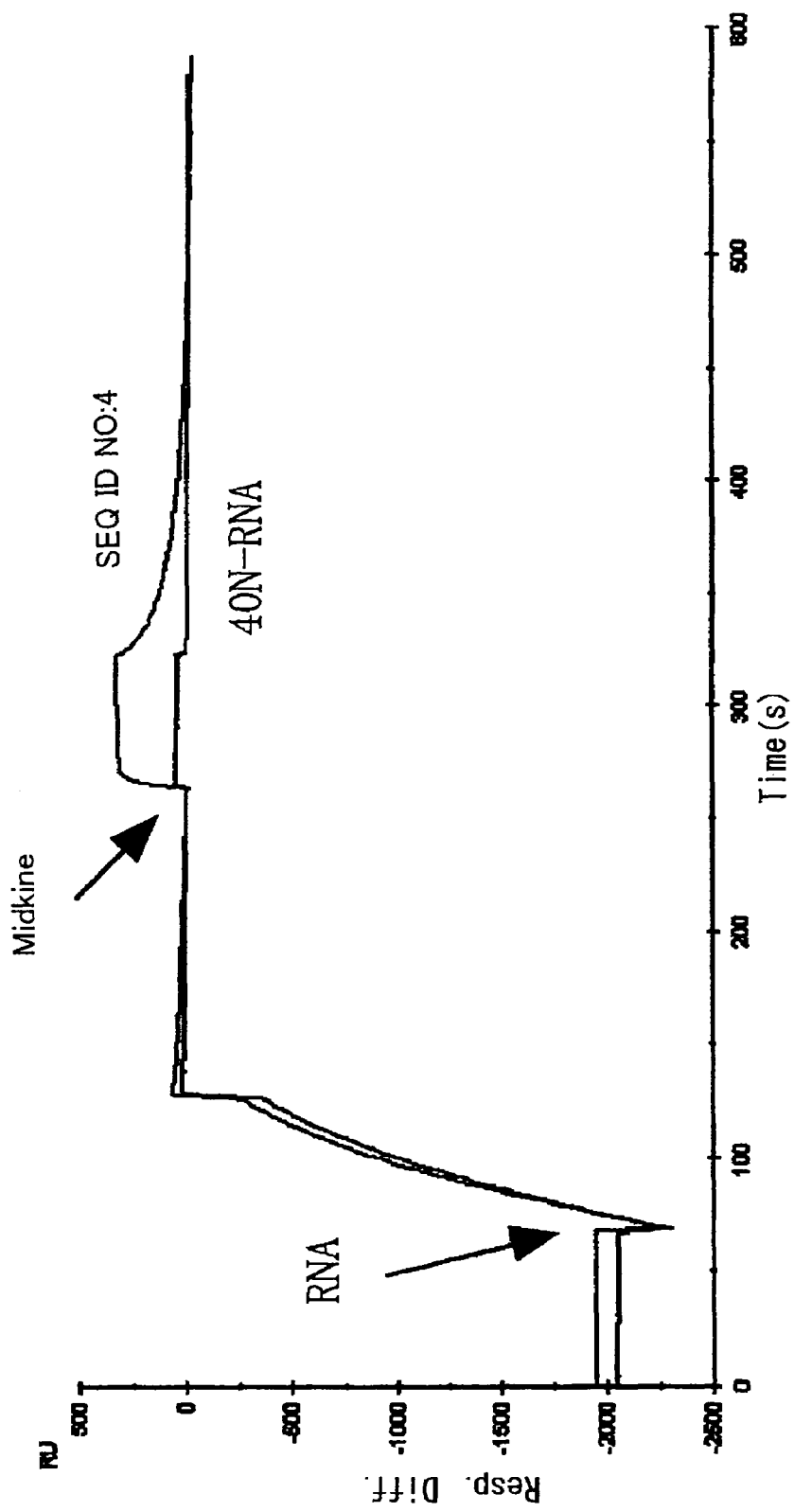
FIG. 7 shows interaction between RNA shown by SEQ ID NO:4 and midkine (sensorgram obtained using BIAcore 2000).

Hence, a measurement was performed using as the running buffer for BIAcore a buffer with a high salt concentration (solution B) prepared by changing the sodium chloride concentration of solution A to 500 mM. It was anticipated that by using the buffer with a high salt concentration, ionic bonding nonspecific adsorption could be reduced. As a result of the measurement, it was found that the 40N-RNA hardly bound to midkine. Meanwhile, the RNAs shown by SEQ ID NO:2 to 5 bound to midkine at higher degrees than with the 40N-RNA (FIG. 7). The fact of binding at the high salt concentration means that the bond is likely to be a hydrophobic bond. This suggests that these RNAs may not be bound nonspecifically to the lysine portion, but specifically recognize midkine.

Next, an experiment was performed in which midkine was immobilized to the CM4 sensor chip by aminocoupling, and the RNA shown by SEQ ID NO:4 or 5, as analyte, was injected, whereby the affinity of RNA and midkine was checked. Midkine immobilization was achieved using N-hydroxysuccinimide (NHS, 11 mg/L) and N-ethyl-N'-(3-dimethylaminopropyl) carbodiimide hydrochloride (EDC, 75 mg/L) per the specifications of BIAcore. Midkine was diluted with HBS-EP buffer (manufactured by BIAcore) and used at a concentration of 20 µg/mL. For blocking, 1 M ethanolamine hydrochloride (pH 8.5) was used. MK (1-59, MK-N, manufactured by Peptide Institute, Inc.) was immobilized to the flow cell 2 of one sensor chip, MK (60-121, MK-C, manufactured by Peptide Institute, Inc.) was immobilized to the flow cell 3, and full-length midkine (MK-NC)was immobilized to the flow cell 4. The flow cell 1 was used as a cell for control. By immobilizing 3 kinds of midkine and midkine fragment to one sensor chip as described above, the affinities for 3 kinds of ligands can be measured at one time. As a result of the measurement, it was found that the RNA shown by SEQ ID NO:4 bound to full-length midkine (hereinafter, written MK-NC) and the C-domain of midkine (hereinafter, written MK-C), but did not bind to the N-domain of midkine (hereinafter, written MK-N) (Table 1). Meanwhile, the RNA shown by SEQ ID NO:5 bound to all of MK-NC, MK-N, and MK-C, but the affinity was higher for MK-N than for MK-C.

TABLE 1

Affinity of midkine and various analytes

| | Midkine | | |
|---|---|---|---|
| | Full-length | MK-N | MK-C |
| SEQ ID NO: 4 | +++ | − | ++ |
| SEQ ID NO: 5 | +++ | ++ | + |
| Heparin | +++ | + | +++ |
| Chondroitin sulfate E | +++ | + | +++ |
| Chondroitin sulfate C | + | − | + |
| tRNA | +++ | − | +++ |

Measured by the surface plasmon resonance method. Midkine was immobilized to the CM4 sensor chip, and various analytes were injected. Affinity is higher in the order of +++, ++, + and −.

Similar experiments were performed using as analyte, in place of RNA, heparin (Heparin, Sodium Salt, Porcine Intestinal Mucosa, Low Molecular Weight, Mw: 5000, manufactured by Calbiochem), chondroitin sulfate E (From Squid cartilage, manufactured by Seikagaku Corporation), chondroitin sulfate C (From Shark cartilage, Mw: 40,000-80,000, manufactured by Seikagaku Corporation), or tRNA (manufactured by Sigma). As a result, it was found that all these analytes had low affinity for MK-N and bound mainly to MK-C (Table 1).

From above, it was found that the RNA shown by SEQ ID NO:4, like heparin and the like, bound to the C domain of midkine. Meanwhile, it was found that the RNA shown by SEQ ID NO:5 had low affinity for the C domain and bound more strongly to the N domain. This shows that the RNAs shown by SEQ ID NO:4 and 5 bind to different sites of midkine. Midkine is known to have in the C domain thereof an active site being a heparin-binding site (Muramatsu H et al., Biochem Biophys Res Commun. 1994 Sep. 15; 203(2):1131-9., 106.; Iwasaki W et al., EMBO J. 1997 Dec. 1; 16(23): 6936-46.).

It was determined whether or not the RNA shown by SEQ ID NO:5 possessed a binding activity for the midkine family protein pleiotrophin by the surface plasmon resonance method as described above. The RNA was immobilized to the SA sensor chip, and 0.5 µM pleiotrophin was injected. To reduce nonspecific adsorption, 0.4 mg/mL tRNA was added to the pleiotrophin solution. As a result of the measurement, it was found that the RNA shown by SEQ ID NO:5 possessed a binding activity for pleiotrophin, but the degree was lower than that for midkine. Using the 40N-RNA as the ligand, a similar measurement was performed. Both midkine and pleiotrophin bound to the 40N-RNA, but the degree was lower than that for the RNA shown by SEQ ID NO:5. The 40N-RNA exhibited higher affinity for midkine than for pleiotrophin. From above, it was found that pleiotrophin, like midkine, possessed a propensity to bind to nucleic acids. It was also found that the RNA shown by SEQ ID NO:5 possessed higher affinity for midkine than for pleiotrophin.

Next, it was determined whether or not the RNAs shown by SEQ ID NO:4 and 5 possessed affinity for other proteins. As the proteins, human IgG1 (manufactured by Calbiochem) and human albumin (manufactured by Sigma) were used. Each RNA was immobilized using the SA sensor chip as described above, and each protein as analyte was injected. As a result, human IgG1 and human albumin did not bind to any of the RNAs shown by SEQ ID NO:4 and 5 at all. From above, it was found that the RNAs shown by SEQ ID NO:4 and 5 did not bind to human albumin and human IgG, which are present in large amounts in the blood.

The binding activities of the RNAs shown by SEQ ID NO:2 to 7, 31, 32, 36, 40, 40-1 and 40-2 with MK were measured. As described above, the measurement was performed with MK immobilized to the CM4 sensor chip. As a result, it was found that all of these RNAs possessed affinity for MK.

EXAMPLE 5

Evaluation of RNA Aptamers by Cell Migration Inhibition Experiment

Midkine is known to possess osteoblast progenitor cell infiltrating action (Qi et al., J. Biol. Chem. 276 (19), 15868-15875, 2001). Hence, it was examined whether or not the prepared RNA aptamers inhibited the cell migration activity of midkine using UMR106 cells of a rat osteoblast progenitor cell line (ATCC No. CRL1661). 30 µL of 1.5 µM midkine was applied to the outer surface of the membrane of Chemotaxicell (membrane pore diameter 8 µm, manufactured by Kurabo) to immobilize the midkine to the outer surface of the membrane. The midkine-immobilized Chemotaxicell was placed on a 24-well culture plate containing 500 µL of a medium (supplemented with 0.3% bovine serum albumin, Dulbecco's Modified Eagle's medium) supplemented with each RNA aptamer added thereto at 100 nM. 200 µL of UMR106 cells were placed in the inner layer of the Chemotaxicell chamber at a density of $1 \times 10^6$ cells/mL, and cultured at 37° C. for 4 hours. The cells remaining in the inner layer of the Chemotaxicell chamber were removed, and the cells that had infiltrated and adhered to the midkine-applied surface were fixed with methanol. The Chemotaxicell chamber was immersed in a 1% aqueous solution of Crystal Violet for 30 minutes to stain the cells. After the Chemotaxicell chamber was washed with distilled water and dried, the pigment was extracted with a mixed solution of 200 µL of 1% SDS and 1% triton X100. 150 µL of the extract was transferred to a 96-well microplate, and its absorbance at 590 nm was determined.

As a result of the measurement, it was found that the RNAs shown by SEQ ID NO:1, 2, 4, and 5 possessed a remarkable cell migration inhibitory activity. The results are shown in Table 2. The aptamer shown by SEQ ID NO:5 exhibited the highest inhibitory activity, the mean for 14 measurements being 76%. The 40N-RNA, used as the negative control, exhibited almost no inhibitory activity.

TABLE 2

Cell migration inhibitory activities of prepared aptamers against midkine and pleiotrophin

| | Midkine | | Pleiotrophin | |
|---|---|---|---|---|
| SEQ ID NO | Inhibitory activity % | Number of measurements | Inhibitory activity % | Number of measurements |
| 1 | 36 | 4 | 0 | 2 |
| 2 | 45 | 4 | — | — |
| 4 | 63 | 6 | 8 | 2 |
| 5 | 76 | 14 | 17 | 6 |
| 40N-RNA | 8 | 6 | 28 | 2 |

RNA concentration: 100 nM

Here, inhibitory activity % is a value obtained by subtracting the number of cells moving with the addition of the aptamer from the number of cells moving without the addition of the aptamer (absorbance of stained cell extract) taken as 100. In the table, each % value is the mean for the number of measurements indicated.

Next, it was measured whether or not the aptamers shown by SEQ ID NO:4 and 5 possessed a cell migration inhibitory activity against pleiotrophin. The experiment was performed as described above, except that pleiotrophin was used in place of midkine. As a result of the experiment, it was found that these aptamers did not exhibit a remarkable inhibitory activity against pleiotrophin (Table 2).

Next, it was measured whether or not heparin, chondroitin sulfate E, chondroitin sulfate C inhibit the cell migration activities of midkine and pleiotrophin. The experiment was performed as described above, except that the aptamers were replaced with heparin, chondroitin sulfate E or chondroitin sulfate C. The supply of heparin used was a product manufactured by Nacalai Tesque. The supplies of chondroitin sulfate E and C used were the same as those used in Example 4. The concentrations of heparin and chondroitin sulfate E were 0.1, 1, 10, and 100 µg/mL. As a result of the experiment, heparin at 0.1 µg/mL inhibited the cell migration activities of midkine and pleiotrophin. At a concentration of 1 µg/mL, heparin inhibited the cell migration activities of midkine and pleiotrophin by not less than 80%. Meanwhile, chondroitin sulfate E at a concentration of 10 µg/mL inhibited midkine by 49%, and pleiotrophin by 69%. Assuming the molecular weight of chondroitin sulfate C to be 40,000, the experiment was performed at 500 nM (20 µg/mL). As a result, when the inhibitory activity of the aptamer shown by SEQ ID NO:4 (500 nM) was taken as 100, the inhibitory activity of chondroitin sulfate C was 44.

From above, it was found that the aptamers shown by SEQ ID NO:1, 2, 4, and 5 bound specifically to midkine to inhibit the cell migration activity thereof. The 40N-RNA nonspecifically adsorbed to midkine electrostatically, but did not inhibit cell migration activity. This shows that the RNAs that had been obtained by SELEX are not attributable to nonspecific adsorption, but bind to an important site associated with the cell migration activity. Heparin and chondroitin sulfate E equivalently inhibited the cell migration activity without distinguishing between midkine and pleiotrophin. Meanwhile, the aptamers shown by SEQ ID NO:4 and 5 inhibited only the activity of midkine. Since midkine and pleiotrophin have a homology of 50%, and also since the heparin-binding site is conserved at a high level, the high specificities of the aptamers are understandable.

EXAMPLE 6

Miniaturization and Stabilization of the Aptamer Shown by SEQ ID NO:4

The aptamer shown by SEQ ID NO:4 is 77 nucleotides long, having the 2' position of the ribose of the pyrimidine nucleotide thereof fluoro-substituted. To enable the chemical synthesis, to reduce the toxicity, and to improve the stability in the blood, miniaturization and stabilization of this aptamer were performed. The operations of miniaturization and stabilization were performed on the basis of the secondary structure estimated by the MFOLD program, and the activity was evaluated by a cell migration inhibition experiment. In the cell migration inhibition experiment, the RNA concentration was 100 nM or 500 nM. Since some errors occur in experimental results depending on cell condition, a previously assayed sample was included as a positive control in each measurement. The inhibitory activities obtained when the RNA concentration was 500 nM are shown in Table 3 (Tables 3-1 and 3-2). The inhibitory activities are expressed as relative values with the activity of the aptamer shown by SEQ ID NO:4 taken as 100, so as to clarify the activity differences among the altered forms. The inhibitory activity % of the aptamer shown by SEQ ID NO:4 (a value obtained by subtracting the number of cells moving with the addition of the aptamer from 100, which is the number of cells moving without the addition of the aptamer) was 73% when the RNA concentration was 500 nM. This is the mean for 4 measurements. The mean for 6 measurements of the inhibitory activity % was 63% when the RNA concentration was 100 nM.

TABLE 3-1

Cell migration inhibitory activities of altered forms of the RNA shown by SEQ ID NO: 4 against midkine

| SEQ ID NO | Activity | Number of measurements | Length (nt) |
|---|---|---|---|
| 4 | 100 | 2 | 77 |
|  | 57 (mouse) | 2 |  |
| 6 | 110 | 2 | 67 |
| 7 | 91 | 2 | 64 |
| 8 | 100 | 2 | 69 |
| 9 | 57 | 2 | 66 |
| 10 | 81 | 2 | 73 |
| 11 | 100 | 2 | 77 |
| 12 | 100 | 2 | 58 |
| 13 | 100 | 2 | 50 |
| 14 | 100 | 2 | 54 |
| 15 | 75 | 2 | 56 |
| 16 | 61 | 2 | 57 |
| 17 | 68 | 2 | 46 |
| 18 | 88 | 2 | 37 |
| 19 | 94 | 2 | 44 |
| 20 | 97 | 2 | 42 |
| 20-1 | 109 | 2 | 42 |
| 20-2 | 84 | 2 | 42 |
| 20-3 | 60 | 2 | 42 |
| 20-4 | 60 | 2 | 42 |
| 20-5 | 88 | 2 | 42 |
| 20-6 | 69 | 2 | 42 |
| 20-7 | 88 | 2 | 42 |
| 20-8 | 99 | 2 | 42 |
| 20-9 | 130 | 2 | 42 |
| 20-10 | 86 | 2 | 42 |
| 20-11 | 76 | 2 | 42 |
| 20-12 | 53 | 2 | 42 |
| 20-13 | 89 | 2 | 42 |

TABLE 3-2

| SEQ ID NO | Activity | Number of measurements | Length (nt) |
|---|---|---|---|
| 21 | 0 | 2 | 44 |
| 22 | 70 | 6 | 33 |
| 23 | 66 | 2 | 38 |
| 24 | 65 | 2 | 38 |
| 25 | 81 | 2 | 41 |
| 26 | 18 | 2 | 41 |
| 27 | 78 | 2 | 41 |
| 28 | 71 | 2 | 31 |
| 29 | 74 | 2 | 31 |
| Cond-C | 44 | 2 |  |

The RNA concentration was 500 nM. The activities are expressed as relative values with the activity of the RNA shown by SEQ ID NO: 4 taken as 100. The inhibitory activity % of the RNA shown by SEQ ID NO: 4 was 73%. This value is the mean for 4 measurements. (mouse) indicates a value relative to mouse midkine. Cond-C indicates chondroitin sulfate C.

The altered parts in the altered forms (SEQ ID NOs:6-29) are explained below.

SEQ ID NO:6: 10 nucleotides were deleted from single stranded part at the 3' end side of RNA shown by SEQ ID NO:4.

gggagaggagaagaggaac(F)gu(F)gc(F)u(F)c(F)u(F)gu(F)ac(F)gaggagu(F)agc(F)c(F)ggaaagaaggc(F)ggu(F)gu(F)gu(F)agaggac(F)a SEQ ID NO:7: 14 nucleotides were deleted from single stranded part at the 5' end side of RNA shown by SEQ ID NO:4, and one G was added for transcription.

gggaac(F)gu(F)gc(F)u(F)c(F)u(F)gu(F)ac(F)gaggagu(F)agc(F)c(F)gg aaagaaggc(F)ggu(F)gu(F)gu(F)agaggac(F)agaau(F)gagga SEQ ID NO:8: 4 base pairs were deleted from the stem at the end side of RNA shown by SEQ ID NO:4.

gggagaggagaagaggaac(F)gc(F)u(F)gu(F)ac(F)gaggagu(F)agc(F)c(F)gg aaagaaggc(F)ggu(F)gu(F)gu(F)agc(F)agaau(F)gagga SEQ ID NO:9: 8 nucleotides from internal loop and CGG on the opposite side thereof were deleted from RNA shown by SEQ ID NO:4.

gggagaggagaagaggaac(F)gu(F)gc(F)u(F)c(F)u(F)gu(F)ac(F)gc(F)c(F) ggaaagaaggu(F)gu(F)gu(F)agaggac(F)agaau(F)gagga SEQ ID NO:10: the loop portion was replaced with GAAA tetra loop in RNA shown by SEQ ID NO:4.

gggagaggagaagaggaac(F)gu(F)gc(F)u(F)c(F)u(F)gu(F)ac(F)gaggagu(F)agc(F)c(F)gaaaggc(F)ggu(F)gu(F)gu(F)agaggac(F)aggaau(F)gagga SEQ ID NO:11: 3 G-U base pairs were replaced with G-C base pairs in the stem at the end side of RNA shown by SEQ ID NO:4.

gggagaggagaagaggaac(F)gu(F)gc(F)u(F)c(F)u(F)gc(F)ac(F)gaggagu(F)agc(F)c(F)ggaaagaaggc(F)ggc(F)gu(F)gc(F)agaggac(F)aggaau(F)gag ga SEQ ID NO:12: three G-U base pairs were replaced with G-C base pairs in the stem at the end side and 11 nucleotides were deleted from single stranded part at the 3' end side of RNA shown by SEQ ID NO:8.

gggagaggagaagaggaac(F)gc(F)u(F)gc(F)ac(F)gaggagu(F)agc(F)c(F)gg aaagaaggc(F)ggc(F)gu(F)gc(F)agc(F)

SEQ ID NO:13: 11 nucleotides were deleted from single stranded part at the 5' end side of RNA shown by SEQ ID NO:12, and GGG was added thereto for transcription.

gggagaggaac(F)gc(F)u(F) gc(F)ac(F)gaggagu(F)agc(F)c(F)ggaaagaagg c(F)ggc(F)gu(F)gc(F)agc(F)

SEQ ID NO:14: one G-C base pair and one C-G base pair were deleted from the stem at the end side of RNA shown by SEQ ID NO: 12.

gggagaggagaagaggaac(F)gc(F)u(F)ac(F)gaggagu(F)agc(F)c(F)ggaaaga aggc(F)ggc(F)gu(F)agc(F)

SEQ ID NO:15: A36 and A37 were deleted from the loop portion of RNA shown by SEQ ID NO:12.

gggagaggagaagaggaac(F)gc(F)u(F)gc(F)ac(F)gaggagu(F)agc(F)c(F)gg aaaggc(F)ggc(F)gu(F)gc(F)agc(F)

SEQ ID NO:16: A23 was deleted from the internal loop portion of RNA shown by SEQ ID NO:12.

gggagaggagaagaggaac(F)gc(F)u(F)gc(F)ac(F)gagggu(F)agc(F)c(F)gga aagaaggc(F)ggc(F)gu(F)gc(F)agc(F)

SEQ ID NO:17: one G-C base pair and one C-G base pair were deleted from the stem at the end side of RNA shown by SEQ ID NO:13.

gggagaggaac(F)gc(F)u(F)ac(F)gaggagu(F)agc(F)c(F)ggaaagaaggc(F)g gc(F)gu(F)agc(F)

SEQ ID NO:18: 11 nucleotides were deleted from single stranded part at the 5' end side of RNA shown by SEQ ID NO:17, and GG was added thereto for transcription.

ggc(F)u(F)ac(F)gaggagu(F)agc(F)c(F)ggaaagaaggc(F)ggc(F)gu(F)ag c(F)

SEQ ID NO:19: one C-G base pair was deleted from stem part at the end side of RNA shown by SEQ ID NO:17.

gggagaggaac(F)gu(F)ac(F)gaggagu(F)agc(F)c(F)ggaaagaaggc(F)ggc(F)gu(F)ac(F)

SEQ ID NO:20: one C-G base pair and one U-A base pair were deleted from stem part at the end side of RNA shown by SEQ ID NO:17.

gggagaggaac(F)gac(F)gaggagu(F)agc(F)c(F)ggaaagaaggc(F)ggc(F)gu(F)c(F)

SEQ ID NO:20-1: single stranded part of RNA shown by SEQ ID NO:20 was entirely modified with OMe.

g(M)g(M)g(M)a(M)g(M)a(M)g(M)g(M)a(M)a(M)c(F)gac(F)gaggagu(F)agc (F)c(F)ggaaagaaggc(F)ggc(F)gu(F)c(F)

SEQ ID NO:20-2: first stem in RNA shown by SEQ ID NO:20 was modified with OMe.
gggagaggaac(F)g(M)a(M)c(F)g(M)aggagu(F)agc(F)c(F)ggaaagaaggc(F) ggc(F)g(M)u(F)c(F)

SEQ ID NO:20-3: second stem in RNA shown by SEQ ID NO:20 was modified with OMe.
gggagaggaac(F)gac(F)gaggagu(F)ag(M)c(F)c(F)ggaaagaag(M)g(M)c(F) ggc(F)gu(F)c(F)

SEQ ID NO:20-4: G in loop part of RNA shown by SEQ ID NO:20 was replaced with OMe.
gggagaggaac(F)gac(F)gaggagu(F)agc(F)c(F)g(M)g(M)aaag(M)aaggc(F) ggc(F)gu(F)c(F)

SEQ ID NO:20-5: A in bulge part of RNA shown by SEQ ID NO:20-1 was replaced with OMe.
g(M)g(M)g(M)a(M)g(M)a(M)g(M)g(M)a(M)a(M)c(F)gac(F)ga(M)gga(M)gu (F)a(M)gc(F)c(F)ggaaagaaggc(F)ggc(F)gu(F)c(F)

SEQ ID NO:20-6: G in bulge part of RNA shown by SEQ ID NO:20-1 was replaced with OMe.
g(M)g(M)g(M)a(M)g(M)a(M)g(M)g(M)a(M)a(M)c(F)gac(F)gag(M)g(M)ag(M)u(F)ag(F)c(F)ggaaagaaggc(F)ggc(F)gu(F)c(F)

SEQ ID NO:20-7: A in loop part of RNA shown by SEQ ID NO:20-1 was modified with OMe.
g(M)g(M)g(M)a(M)g(M)a(M)g(M)g(M)a(M)a(M)c(F)gac(F)gaggagu(F)agc (F)c(F)gga(M)aa(M)gaaggc(F)ggc(F)gu(F)c(F)

SEQ ID NO:20-8: A in loop part of RNA shown by SEQ ID NO:20-5 was modified with OMe.
g(M)g(M)g(M)a(M)g(M)a(M)g(M)g(M)a(M)a(M)c(F)gac(F)ga(M)gga(M)gu (F)a(M)gc(F)c(F)gga(M)aa(M)gaaggc(F)ggc(F)gu(F)c(F)

SEQ ID NO:20-9: first stem in RNA shown by SEQ ID NO:20-5 was modified with OMe.
g(M)g(M)g(M)a(M)g(M)a(M)g(M)g(M)a(M)a(M)c(F)g(M)a(M)c(F)ga(M)gg a(M)gu(F)a(M)gc(F)c(F)ggaaa-gaaggc(F)ggc(F)g(M)u(F)c(F)

SEQ ID NO:20-10: some parts of RNA shown by SEQ ID NO:20-5 were modified with OMe.
g(M)g(M)g(M)a(M)g(M)a(M)g(M)g(M)a(M)a(M)c(F)gac(F)ga(M)gga(M)gu (F)a(M)gc(F)c(F)ggaaagaaggc(F)g(M)g(M)c(F)gu(F)c(F)

SEQ ID NO:20-11: some parts of RNA shown by SEQ ID NO:20-5 were modified with OMe.
g(M)g(M)g(M)a(M)g(M)a(M)g(M)g(M)a(M)a(M)c(F)g(M)a(M)c(F)ga(M)gg a(M)gu(F)a(M)gc(F)c(F)gga(M)aa(M)gaaggc(F)g(M)g(M)c(F)g(M)u(F)c (F)

SEQ ID NO:20-12: some parts of RNA shown by SEQ ID NO:20-5 were modified with OMe.
g(M)g(M)g(M)a(M)g(M)a(M)g(M)g(M)a(M)a(M)c(F)g(M)a(M)c(F)ga(M)gg a(M)gu(F)a(M)gc(F)c(F)gga(M)aa(M)g(M)aaggc(F)ggc(F)g(M)u(F)c(F)

SEQ ID NO:20-13: some parts of RNA shown by SEQ ID NO:20-5 were modified with OMe.
g(M)g(M)g(M)a(M)g(M)a(M)g(M)g(M)a(M)a(M)c(F)g(M)a(M)c(F)ga(M)gg a(M)gu(F)a(M)gc(F)c(F)gga(M)aa(M)gaag(M)gc(F)ggc(F)g(M)u(F)c(F)

SEQ ID NO:21: one G-C base pair was deleted from stem part at the loop side of RNA shown by SEQ ID NO:17.
gggagaggaac(F)gc(F)u(F)ac(F)gaggagu(F)agc(F)ggaaa-gaagc(F)ggc(F) gu(F)agc(F)

SEQ ID NO:22: 11 nucleotides were deleted from single stranded part at the 5' end side of RNA shown by SEQ ID NO:20, and two Gs were added for transcription.
gggac(F)gaggagu(F)agc(F)c(F)ggaaagaaggc(F)ggc(F)gu(F)c(F)

SEQ ID NO:23: the loop portion was replaced with GAAA tetra loop in RNA shown by SEQ ID NO:20.
gggagaggaac(F)gac(F)gaggagu(F)agc(F)c(F)gaaaggc(F)ggc(F)gu(F)c(F)

SEQ ID NO:24: the loop portion was replaced with UUCG tetra loop in RNA shown by SEQ ID NO:20.
gggagaggaac(F)gac(F)gaggagu(F)agc(F)tc(F)u(F)u(F)c(F)gggc(F)ggc(F)gu(F)c(F)

SEQ ID NO:25: the internal loop portion in RNA shown by SEQ ID NO:20 was replaced with the internal loop of aptamer shown by SEQ ID NO:2.
gggagaggaac(F)gac(F)gagaac(F)agc(F)c(F)ggaaagaaggc(F)ggc(F)gu(F)c(F)

SEQ ID NO:26: G18 of internal loop in RNA shown by SEQ ID NO:20 was deleted.
gggagaggaac(F)gac(F)gagagu(F)agc(F)c(F)ggaaagaaggc(F)ggc(F)gu(F)c(F)

SEQ ID NO:27: A19 of internal loop in RNA shown by SEQ ID NO:20 was deleted.
gggagaggaac(F)gac(F)gagggu(F)agc(F)c(F)ggaaagaaggc(F)ggc(F)gu(F)c(F).

SEQ ID NO:28: two G were removed from the 5' end and the second base pair A-U was changed to G-C in RNA shown by SEQ ID NO:22.
ggc(F)gaggagu(F)agc(F)c(F)ggaaagaaggc(F)ggc(F)gc(F)c(F)

SEQ ID NO:29: two G were removed from the 5' end of RNA shown by SEQ ID NO:22.
gac(F)gaggagu(F)agc(F)c(F)ggaaagaaggc(F)ggc(F)gu(F)c(F)

The cell migration inhibitory activity of the aptamer shown by SEQ ID NO:4 against mouse midkine was examined. The experimental method was the same as that for the above-described experiment on human midkine. As a result of the experiment, the inhibitory activity % of this aptamer was 50%. This is equivalent to about 57 relative to the inhibitory activity of this aptamer against human midkine taken as 100; the activity decreased evidently, compared with the inhibitory activity against human midkine. Thus, this aptamer was found to be an aptamer that exhibits a higher inhibitory activity against human midkine.

As shown in Table 3, the aptamer shown by SEQ ID NO:4, which was originally 77 nucleotides long, could be miniaturized to 31 nucleotides, without considerably reducing the activity (SEQ ID NO:28, 29). The hairpin loop portion of this aptamer obtained need not always be GGAAAGAA; the aptamer retained the activity even when the hairpin loop portion was the GAAA or UUCG tetra-loop (SEQ ID NO:23, 24). Even when the internal loop portion was replaced with the internal loop portion of the aptamer shown by SEQ ID NO:2, the activity was retained (SEQ ID NO:25). Even when A19 was deleted, the activity was retained, but when G18 was deleted, the activity decreased extremely (SEQ ID NO:26, 27). Meanwhile, it was found that when the C-G base pair of the stem on the loop side was deleted, the secondary structure changed widely and the inhibitory activity was lost (SEQ ID NO:21). From above, it was found that the 42-nucleotide aptamer shown by SEQ ID NO:20 (FIG. 8) retained the activity even after some nucleotides are replaced with other nucleotides or deleted, provided that the basic structure thereof did not change widely.

EXAMPLE 7

Miniaturization and Stabilization of the Aptamer Shown by SEQ ID NO:5

The aptamer shown by SEQ ID NO:5 is 77 nucleotides long, having the 2'-position of the ribose of the pyrimidine nucleotide fluoro-substituted. To enable the chemical synthesis, to reduce the toxicity, and to improve the stability in the blood, miniaturization and stabilization of this aptamer were performed. The operations of miniaturization and stabilization were performed on the basis of the secondary structure estimated by the MFOLD program, and the activity was evaluated by a cell migration inhibition experiment. The RNA concentration in the cell migration inhibition experiment was 100 nM or 500 nM. Since some errors occur in experimental results depending on cell condition, a previously assayed sample was included as a positive control in each measurement. The inhibitory activities obtained when the RNA concentration was 100 nM are shown in Table 4-1. The inhibitory activities are expressed as relative values with the activity of the aptamer shown by SEQ ID NO:5 taken as 100, so as to clarify the activity differences among the altered forms. The inhibitory activity % of the aptamer shown by SEQ ID NO:5 (a value obtained by subtracting the number of cells moving with the addition of the aptamer from 100, which is the number of cells moving without the addition of the aptamer) was 76% when the RNA concentration was 100 nM. This is the mean for 14 measurements. With the RNA concentration changed to 500 nM, a similar experiment was performed. The results are shown in Table 4-2 (Table 4-2-1, Table 4-2-2). Activities are expressed as relative values with the activity of the aptamer shown by SEQ ID NO:40 taken as 100. The inhibitory activity % of the aptamer shown by SEQ ID NO:40 was 82%. This is the mean for 4 measurements.

TABLE 4-1

| SEQ ID NO | Midkine activity | Number of measurements | Pleiotrophin activity | Number of measurements | length (nt) |
|---|---|---|---|---|---|
| 5 | 100 | 14 | 13 | 6 | 77 |
| 30 | 44 | 2 | — | — | 71 |
| 31 | 94 | 6 | 17 | 4 | 67 |
| 32 | 100 | 6 | 11 | 4 | 57 |
| 33 | 40 | 6 | 5 | 4 | 61 |
| 34 | 0 | 2 | — | — | 46 |
| 35 | 90 | 4 | 0 | 2 | 51 |
| 36 | 91 | 4 | 27 | 2 | 53 |
| 36-1 | 60 | 4 | 0 | 2 | 53 |
| 37 | 0 | 2 | — | — | 49 |
| 38 | 0 | 2 | — | — | 57 |
| 39 | 52 | 2 | — | — | 45 |
| 40 | 98 | 4 | 0 | 2 | 49 |
| 40-1 | 80 | 2 | — | — | 49 |
| 40-2 | 31 | 2 | — | — | 49 |
| 40-3 | 65 | 2 | — | — | 49 |
| 41 | 97 | 4 | 8.1 | 2 | 52 |
| 42 | 110 | 4 | 8.7 | 2 | 52 |
| 43 | 42 | 2 | — | — | 52 |

The RNA concentration was 100 nM. The activities are expressed as relative values with the inhibitory activity of the RNA shown by SEQ ID NO: 5 against midkine taken as 100. The inhibitory activity % of the RNA shown by SEQ ID NO: 5 against midkine was 76%. This value is the mean for 14 measurements.

TABLE 4-2-1

| SEQ ID NO | Activity | Number of measurements | Length (nt) |
|---|---|---|---|
| 40 | 100 | 2 | 49 |
| 40-1 | 99 | 2 | 49 |
| 40-2 | 88 | 2 | 49 |
| 40-3 | 100 | 2 | 49 |
| 44 | 100 | 2 | 47 |
| 45 | 100 | 2 | 45 |
| 45-1 | 100 | 2 | 45 |
| 45-2 | 100 | 2 | 45 |
| 45-3 | 56 | 2 | 45 |
| 45-4 | 100 | 2 | 45 |
| 45-4-1 | 98* | 2 | 45 |
| 45-4-1-1 | 85* | 2 | 45 |
| 46 | 92 | 2 | 49 |
| 47 | 84 | 2 | 48 |
| 48 | 60 | 2 | 48 |
| 49 | 69 | 2 | 48 |
| 50 | 91 | 2 | 43 |
| 51 | 100 | 2 | 51 |
| 52 | 100 | 2 | 51 |
| 53 | 100 | 2 | 51 |
| 54 | 100 | 2 | 45 |
| 55 | 100 | 2 | 43 |
| 56 | 100 | 2 | 43 |
| 57 | 100 | 2 | 43 |
| 58 | 100 | 2 | 43 |
| 59 | 53 | 2 | 29 |
| 60 | 70 | 2 | 35 |

TABLE 4-2-2

| SEQ ID NO | Activity | Number of measurements | Length (nt) |
|---|---|---|---|
| 61 | 100 | 2 | 39 |
| 61-1 | 45* | 2 | 39 |
| 61-2 | 55* | 2 | 39 |
| 61-3 | 80 | 2 | 39 |
| 61-4 | 86 | 4 | 39 |
| 61-5 | 40 | 4 | 39 |
| 61-6 | 57 | 2 | 39 |
| 61-7 | 46 | 2 | 39 |
| 61-8 | 54 | 4 | 39 |
| 61-9 | 39 | 2 | 39 |
| 62 | 44 | 2 | 39 |
| 63 | 97 | 2 | 45 |
| 64 | 55* | 2 | 37 |
| 65 | 0 | 2 | 39 |
| 66 | 51 | 2 | 38 |
| 67 | 110 | 2 | 38 |
| 68 | 72 | 2 | 39 |
| 69 | 60 | 2 | 39 |
| 70 | 110 | 2 | 39 |
| tRNA | 28 | 2 | |
| Thrombin-S | 0 | 2 | |
| HIV-S | 48 | 2 | |

The RNA concentration was 500 nM. The activities are expressed as relative values with the inhibitory activity of the RNA shown by SEQ ID NO: 40 against midkine taken as 100. The inhibitory activity % of the RNA shown by SEQ ID NO: 40 against midkine was 82%. These values are means for 4 measurements.
*tentatively identified value The altered parts in the altered forms (SEQ ID NOs:30-70) are explained below.

SEQ ID NO:30: 6 nucleotides were deleted from single stranded part at the 5' end side of RNA shown by SEQ ID NO:5, and one G was added for transcription.

ggagaagaggaagu(F)gu(F)gc(F)ac(F)aggggu(F)u(F)ggu(F)gu(F)c(F)ggg u(F)gc(F)au(F)ac(F)agu(F)au(F)aagau(F)agaggac(F)aggaau(F)gagga SEQ ID NO:31: 10 nucleotides were deleted from single stranded part at the 3' end side of RNA shown by SEQ ID NO:5.

gggagaggagaagaggaagu(F)gu(F)gc(F)ac(F)aggggu(F)u(F) ggu(F)gu(F)c (F)gggu(F)gc(F)au(F)ac(F)agu(F)au(F)aa- gau(F)agaggac(F)a SEQ ID NO:32: 20 nucleotides were deleted from single stranded part at the 3' end side of RNA shown by SEQ ID NO:5.

gggagaggagaagaggaagu(F)gu(F)gc(F)ac(F)aggggu(F)u(F) ggu(F)gu(F)c (F)gggu(F)gc(F)au(F)ac(F)agu(F)au(F)aag SEQ ID NO:33: 6 nucleotides were deleted from single stranded part at the 5' end side and 10 nucleotides were deleted from single stranded part at the 3' end side of RNA shown by SEQ ID NO:5.

ggagaagaggaagu(F)gu(F)gc(F)ac(F)aggggu(F)u(F)ggu(F)gu (F)c(F)ggg u(F)gc(F)au(F)ac(F)agu(F)au(F)aagau(F) agaggac(F)a SEQ ID NO:34: 12 nucleotides were deleted from single stranded part at the 5' end side and 20 nucleotides were deleted from single stranded part at the 3' end side of RNA shown by SEQ ID NO:5.

ggaggaagu(F)gu(F)gc(F)ac(F)agggu(F)u(F)ggu(F)gu(F)c (F)gggu(F)g c(F)au(F)ac(F)agu(F)au(F)aag SEQ ID NO:35: 6 nucleotides were deleted from single stranded part at the 3' end side of RNA shown by SEQ ID NO:32.

gggagaggagaagaggaagu(F)gu(F)gc(F)ac(F)aggggu(F)u(F) ggu(F)gu(F)c (F)gggu(F)gc(F)au(F)ac(F)ag SEQ ID NO:36: two base pairs were deleted from the stem at the end side of RNA shown by SEQ ID NO:32.

gggagaggagaagaggaagu(F)gc(F)ac(F)aggggu(F)u(F)ggu(F) gu(F)c(F)gg gu(F)gc(F)ac(F)agu(F)au(F)aag SEQ ID NO:36-1: single stranded part at the 5' end side of RNA shown by SEQ ID NO:36 was entirely modified with OMe.

g(M)g(M)g(M)a(M)g(M)a(M)g(M)g(M)a(M)g(M)a(M)a (M)g(M)a(M)g(M)g(M)a(M)a(M)gu(F)gc(F)ac(F) aggggu(F)u(F)ggu(F)gu(F)c(F)gggu(F)gc(F)ac(F)agu(F) au(F)aag SEQ ID NO:37: four base pairs were deleted from the stem at the end side of RNA shown by SEQ ID NO:32.

gggagaggagaagaggaagc(F)ac(F)aggggu(F)u(F)ggu(F)gu(F) c(F)gggu(F) gc(F)agu(F)au(F)aag SEQ ID NO:38: single stranded part at the 5' end side of RNA shown by SEQ ID NO:32 was changed to poly U where U shows fluorinated ribose at 2'-position.

gggu(F)u(F)u(F)u(F)u(F)u(F)u(F)u(F)u(F)u(F)u(F)u(F) u(F)u(F) gu(F)gu(F)gc(F)ac(F)aggggu(F)u(F)ggu(F)gu (F)c(F)gggu(F)gc(F)au(F)ac(F)agu(F)au(F)aag SEQ ID NO:39: 6 nucleotides were deleted from single stranded part at the 3' end side and one base pair was deleted from the stem at the end side of RNA shown by SEQ ID NO:36.

gggagaggagaagaggaaggc(F)ac(F)aggggu(F)u(F)ggu(F)gu (F)c(F)gggu(F)gc(F)c(F)ag

SEQ ID NO:40: 8 nucleotides were deleted from single stranded part at the 3' end side of RNA shown by SEQ ID NO:36.

gggagaggagaagaggaagu(F)gu(F)gc(F)ac(F)aggggu(F)u(F) ggu(F)gu(F)c (F)gggu(F)gc(F)au(F)ac(F)

SEQ ID NO:40-1: polyethylene glycol with molecular weight of 2000 was added to the 5' end via C12 linker and idT was added to the 3' end of RNA shown by SEQ ID NO:40.

PEG2000-C12-gggagaggagaagaggaagu(F)gu(F)gc(F)ac(F) aggggu(F)u(F)ggu(F)gu(F)c (F)gggu(F)gc(F)au(F)ac(F)- idT SEQ ID NO:40-2: All G in single stranded part at the 5' end side of RNA shown by SEQ ID NO:40 was modified with OMe.

g(M)g(M)g(M)ag(M)ag(M)g(M)ag(M)aag(M)ag(M)g(M) aagu(F)gu(F)gc(F) ac(F)aggggu(F)u(F)ggu(F)gu(F)c(F) gggu(F)gc(F)au(F)ac(F)

SEQ ID NO:40-3: All A in single stranded part at the 5' end side of RNA shown by SEQ ID NO:40 was entirely modified with OMe.

ggga(M)ga(M)gga(M)ga (M)a(M)ga(M)gga(M)a(M)gu(F) gu(F)gc(F)ac(F)a ggggu(F)u(F)ggu(F)gu(F)c(F)gggu(F) gc(F)au(F)ac(F)

SEQ ID NO:41: G5 was deleted from single stranded part at the 5' end side of RNA shown by SEQ ID NO:36.

gggaaggagaagaggaagu(F)gc(F)ac(F)aggggu(F)u(F)ggu(F) gu(F)c(F)ggg u(F)gc(F)ac(F)agu(F)au(F)aag SEQ ID NO:42: A11 was deleted from single stranded part at the 5' end side of RNA shown by SEQ ID NO:36.

gggagaggagagaggaagu(F)gc(F)ac(F)aggggu(F)u(F)ggu(F) gu(F)c(F)ggg u(F)gc(F)ac(F)agu(F)au(F)aag SEQ ID NO:43: A17 was deleted from single stranded part at the 5' end side of RNA shown by SEQ ID NO:36.

gggagaggagaagaggagu(F)gc(F)ac(F)aggggu(F)u(F)ggu(F) gu(F)c(F)ggg u(F)gc(F)ac(F)agu(F)au(F)aag SEQ ID NO:44: one base pair was deleted from the stem at the end side of RNA shown by SEQ ID NO:40.

gggagaggagaagaggaagu(F)u(F)gc(F)ac(F)aggggu(F)u(F) ggu(F)gu(F)c(F)gggu(F)gc(F)aac(F)

SEQ ID NO:45: two base pairs were deleted from the stem at the end side of RNA shown by SEQ ID NO:40.

gggagaggagaagaggaagu(F)gc(F)ac(F)aggggu(F)u(F)ggu(F) gu(F)c(F)gg gu(F)gc(F)ac(F)

SEQ ID NO:45-1: polyethylene glycol with molecular weight of 2000 was added to the 5' end via C12 linker and idT was added to the 3' end of RNA shown by SEQ ID NO:45.

PEG2000-C12-ggga(M)ga(M)gga(M)ga(M)a(M)ga(M)gga (M)a(M)gu(F)gc(F)ac(F)aggggu (F)u(F)ggu(F)gu(F)c(F) gggu(F)gc(F)ac(F)-idT SEQ ID NO:45-2: all A in single stranded part and all G in loop part at the 5' end side of RNA shown by SEQ ID NO:45 were entirely modified with OMe.

ggga(M)ga(M)gga(M)ga(M)a(M)ga(M)gga(M)a(M)gu(F) gc(F)ac(F)agggg(M)u(F)u(F)g(M)g(M)u(F)g(M)u(F)c(F) gggu(F)gc(F)ac(F)

SEQ ID NO:45-3: all A in single stranded part and all A and G in internal loop part at the 5' end side of RNA shown by SEQ ID NO:45 were entirely modified with OMe.

ggga(M)ga(M)gga(M)ga(M)a(M)ga(M)gga(M)a(M)gu(F) gc(F)ac(F)a(M)g(M)gggu(F)u(F)ggu(F)gu(F)c(F)g(M)g (M)gu(F)gc(F)ac(F)

SEQ ID NO:45-4: all A in single stranded part at the 5' end side and all A and G in stem part at the end side of RNA shown by SEQ ID NO:45 were entirely modified with OMe.

ggga(M)ga(M)gga(M)ga(M)a(M)ga(M)gga(M)a(M)gu(F)g (M)c(F)a(M)c(F) aggggu(F)u(F)ggu(F)gu(F)c(F)gggu(F) g(M)c(F)a(M)c(F)

SEQ ID NO:45-4-1: all G in loop part of RNA shown by SEQ ID NO:45-4 was entirely modified with OMe.

ggga(M)ga(M)gga(M)ga(M)a(M)ga(M)gga(M)a(M)g(M)u (F)g(M)c(F)a(M)c (F)aggg(M)g(M)u(F)u(F)g(M)g(M)u (F)g(M)u(F)c(F)gggu(F)g(M)c(F)a(M)c(F)

SEQ ID NO:45-4-1-1: C24 of RNA shown by SEQ ID NO:45-4-1 was changed to RNA nucleotide.

ggga(M)ga(M)gga(M)ga(M)a(M)ga(M)gga(M)a(M)g(M)u (F)g(M)c(F)a(M)c aggg(M)g(M)u(F)u(F)g(M)g(M)u(F)g (M)u(F)c(F)gggu(F)g(M)c(F)a(M)c (F)

SEQ ID NO:46: A-U base pair was replaced with G-C base pair in the stem at the end side of RNA shown by SEQ ID NO:40.

gggagaggagaagaggaagu(F)gc(F)gc(F)gc(F)aggggu(F)u(F) ggu(F)gu(F)c (F)gggc(F)gc(F)gu(F)ac(F)

SEQ ID NO:47: U32 was deleted from the loop of RNA shown by SEQ ID NO:40.

gggagaggagaagaggaagu(F)gu(F)gc(F)ac(F)aggggu(F)ggu (F)gu(F)c(F)g ggu(F)gc(F)au(F)ac(F)

SEQ ID NO:48: G34 was deleted from the loop of RNA shown by SEQ ID NO:40.

gggagaggagaagaggaagu(F)gu(F)gc(F)ac(F)aggggu(F)u(F) gu(F)gu(F)c(F)gggu(F)gc(F)au(F)ac(F)

SEQ ID NO:49: U36 was deleted from the loop of RNA shown by SEQ ID NO:40.

gggagaggagaagaggaagu(F)gu(F)gc(F)ac(F)aggggu(F)u(F) gggu(F)c(F)g ggu(F)gc(F)au(F)ac(F)

SEQ ID NO:50: G4 and G10 were deleted from single stranded part at the 5' end side of RNA shown by SEQ ID NO:45.

gggaaggaaagaggaagu (F) gc(F) ac(F) aggggu(F)u(F) ggu(F) gu (F) c (F) gggu (F)gc(F)ac(F)

SEQ ID NO:51: G5 and A11 were deleted from single stranded part at the 5' end side of RNA shown by SEQ ID NO:36.

gggaaggagagaggaagu(F)gc(F)ac(F)aggggu(F)u(F)ggu(F)gu (F)c(F)gggu (F)gc(F)ac(F)agu(F)au(F)aag SEQ ID NO:52: G1 and G5 were deleted from single stranded part at the 5' end side of RNA shown by SEQ ID NO:36.

ggaaggagaagaggaagu(F)gc(F)ac(F)aggggu(F)u(F)ggu(F)gu (F)c(F)gggu (F)gc(F)ac(F)agu(F)au(F)aag SEQ ID NO:53: G5 and G10 were deleted from single stranded part at the 5' end side of RNA shown by SEQ ID NO:36.

gggaaggaaagaggaagu(F)gc(F)ac(F)aggggu(F)u(F)ggu(F)gu (F)c(F)gggu (F)gc(F)ac(F)agu(F)au(F)aag SEQ ID NO:54: all G was modified with F and all A was modified with OMe in single stranded part at the 5' end side of RNA shown by SEQ ID NO:45.

g(F)g(F)g(F)a(M)g(F)a(M)g(F)g(F)a(M)g(F)a(M)a(M)g(F) a(M)g(F)g(F)a(M)a(M)gu(F)gc(F)ac(F)aggggu(F)u(F) ggu(F)gu(F)c(F)gggu(F)gc(F)ac(F)

SEQ ID NO:55: A11 and A12 were deleted from single stranded part at the 5' end side of RNA shown by SEQ ID NO:45.

gggagaggaggaggaagu(F)gc(F)ac(F)aggggu(F)u(F)ggu(F)gu (F)c(F)gggu (F)gc(F)ac(F) SEQ ID NO:56: G13 and A14 were deleted from single stranded part at the 5' end side of RNA shown by SEQ ID NO:45.

gggagaggagaaggaagu(F)gc(F)ac(F)aggggu(F)u(F)ggu(F)gu (F)c(F)gggu (F)gc(F)ac(F)

SEQ ID NO:57: G15 and G16 were deleted from single stranded part at the 5' end side of RNA shown by SEQ ID NO:45.

gggagaggagaagaaagu(F)gc(F)ac(F)aggggu(F)u(F)ggu(F)gu (F)c(F)gggu (F)gc(F)ac(F)

SEQ ID NO:58: A17 and A18 were deleted from single stranded part at the 5' end side of RNA shown by SEQ ID NO:45.

gggagaggagaagagggu(F)gc(F)ac(F)aggggu(F)u(F)ggu(F)gu (F)c(F)gggu (F)gc(F)ac(F)

SEQ ID NO:59: 18 nucleotides were deleted from single stranded part at the 5' end side of RNA shown by SEQ ID NO:45, and two Gs were added for transcription.

gggu(F)gc(F)ac(F)aggggu(F)u(F)ggu(F)gu(F)c(F)gggu(F) gc(F)ac(F)

SEQ ID NO:60: single stranded part at the 5' end side of RNA shown by SEQ ID NO:45 was changed to GGGAAGGA.

gggaaggagu(F)gc(F)ac(F)aggggu(F)u(F)ggu(F)gu(F)c(F) gggu(F)gc(F) ac(F)

SEQ ID NO:61: G5, G10, A11, A12, G13 and A14 were deleted from single stranded part at the 5' end side of RNA shown by SEQ ID NO:45.

gggaaggaggaagu(F)gc(F)ac(F)aggggu(F)u(F)gggi(F)gu(F)c (F)gggu(F)g c(F)ac(F)

SEQ ID NO:61-1: G was modified with DNA nucleotide and A was modified with OMe in single stranded part, and G in loop part was modified with OMe at the 5' end side of RNA shown by SEQ ID NO:61.

g(H)g(H)g(H)a(M)a(M)g(H)g(H)a(M)g(H)g(H)a(M)a(M) gu(F)gc(F)ac(F) aggggu(F)u(F)ggu(F)gu(F)c(F)gggu(F) gc(F)ac(F)

SEQ ID NO:61-2: G and A in single stranded part and G in loop part at the 5' end side of RNA shown by SEQ ID NO:61 were modified with OMe.

g(M)g(M)g(M)a(M)a(M)g(M)g(M)a(M)g(M)g(M)a(M)a (M)gu(F)gc(F)ac(F) aggggu(F)u(F)ggu(F)gu(F)c(F)gggu (F)gc(F)ac(F)

SEQ ID NO:61-3: some part of RNA shown by SEQ ID NO:61 were modified with F and OMe.

g(F)g(F)g(F)a(M)a(M)g(F)g(F)a(M)g(F)g(F)a(M)a(M)g (M)u(F)g(M)c(F)a(M)c(F)a(M)g(F)g(M)g(M)g(M)u(F)u (F)g(M)g(M)u(F)g(M)u(F)c(F)g(F)g(F)g(M)u(F)g(M)c (F)a(M)c(F)

SEQ ID NO:61-4: some part of RNA shown by SEQ ID NO:61 were modified with OMe.

ggga(M)a (M) gga(M)gga(M)a(M)g(M)u(F)g(M)c(F) a(M) c(F)aggg(M) g(M)u (F)u(F)g(M)g(M)u(F)g(M)u(F)c(F) gggu(F)g(M)c(F)a(M)c(F)

SEQ ID NO:61-5: branched 40 kDa polyethylene glycol chain was added to the 5' end and idT was added to the 3' end of RNA shown by SEQ ID NO:61-5.

PEG40k-ggga(M)a(M)gga(M)gga(M)a(M)g(M)u(F)g(M)c (F)a(M)c(F)aggg(M)g(M)u (F)u(F)g(M)g(M)u(F)g(M)u (F)c(F)gggu(F)g(M)c(F)a(M)c(F)-idT SEQ ID NO:61-6: 30 kDa polyethylene glycol chain was added to the both ends of RNA shown by SEQ ID NO:61-5.

PEG30k-ggga(M)a(M)gga(M)gga(M)a(M)g(M)u(F)g(M)c (F)a(M)c(F)aggg(M)g(M)u (F)u(F)g(M)g(M)u(F)g(M)u (F)c(F)gggu(F)g(M)c(F)a(M)c(F)-PEG30k SEQ ID NO:61-7: some part of RNA shown by SEQ ID NO:61 were modified with OMe.

ggga(M)a(M)gga(M)gga(M)a(M)g(M)u(F)g(M)c(F)a(M)c (F)aggg(M)g(M)u (F)u(F)g(M)g(M)u(F)g(M)u(F)c(F)g (M)g(M)gu(F)g(M)c(F)a(M)c(F)

SEQ ID NO:61-8: some part of RNA shown by SEQ ID NO:61 were modified with OMe.

ggga(M)a(M)gga(M)gga(M)a(M)g(M)u(F)g(M)c(F)a(M)c (F)a(M)g(M)gg(M)g(M)u(F)u(F)g(M)g(M)u(F)g(M)u(F) c(F)gggu(F)g(M)c(F)a(M)c(F)

SEQ ID NO:61-9: some part of RNA shown by SEQ ID NO:61 were modified with OMe and 2 kDa polyethylene glycol was added to the 5' end.

PEG2000-ggga(M)a(M)gga(M)gga(M)a(M)g(M)u(F)g(M)c (F)a(M)c(F)a(M)gg(M)g(M)g(M)u(F)u(F)g(M)g(M)u(F) g(M)u(F)c(F)ggg(M)u(F)g(M)c(F)a(M)c(F)

SEQ ID NO:62: G13, A14, G15, G16, A17 and A18 were deleted from single stranded part at the 5' end side of RNA shown by SEQ ID NO:45.

gggagaggagaagu(F)gc(F)ac(F)aggggu(F)u(F)ggu(F)gu(F)c (F)gggu(F)g c(F)ac(F)

SEQ ID NO:63: A25 and G26 in RNA shown by SEQ ID NO:45 were changed to C to make internal loop as stem.

gggagaggagaagaggaagu(F)gc(F)ac(F)c(F)c(F)gggu(F)u(F) ggu(F)gu(F) c(F)gggu(F)gc(F)ac(F)

SEQ ID NO:64: U-A was deleted from the stem at the 5' end side of RNA shown by SEQ ID NO:61.

gggaaggaggaaggc(F)ac(F)aggggu(F)u(F)ggu(F)gu(F)c(F) gggu(F)gc(F) c(F)

SEQ ID NO:65: A19 and G20 in the internal loop of RNA shown by SEQ ID NO:61 were replaced with C.
gggaaggaggaagu(F)gc(F)ac(F)c(F)c(F)gggu(F)u(F)ggu(F) gu(F)c(F)gg gu(F)gc(F)ac(F)

SEQ ID NO:66: some part of RNA shown by SEQ ID NO:61 were modified with OMe and G was modified with F.
g(F)g(F)a(M)a(M)g(F)g(F)a(M)g(F)g(F)a(M)a(M)g(M)u (F)g(M)c(F)a(M)c(F)a(M)gg(M)g(M)g(M)u(F)u(F)g(M) g(M)u(F)g(M)u(F)c(F)g(F)g(F)g (M)u(F)g(M)c(F)a(M)c (F)

SEQ ID NO:67: modification of RNA shown by SEQ ID NO:66 was changed.
gga(M)a(M)gga(M)gga(M)a(M)g(M)u(F)g(M)c(F)a(M)c (F)aggg(M)g(M)u(F)u(F)g(M)g(M)u(F)g(M)u(F)c(F) gggu(F)g(M)c(F)a(M)c(F)

SEQ ID NO:68: some part of RNA shown by SEQ ID NO:61 were modified with OMe and U28 was replaced with A(M).
ggga(M)a(M)gga(M)gga(M)a(M)g(M)u(F)g(M)c(F)a(M)c (F)aggg(M)g(M)u (F)u(F)g(M)g(M)a(M)g(M)u(F)c(F) gggu(F)g(M)c(F)a(M)c(F)

SEQ ID NO:69: some part of RNA shown by SEQ ID NO:61 were modified with OMe and U25 was replaced with A(M).
ggga(M)a(M)gga(M)gga(M)a(M)g(M)u(F)g(M)c(F)a(M)c (F)aggg(M)g(M)u (F)a(M)g(M)g(M)u(F)g(M)u(F)c(F) gggu(F)g(M)c(F)a(M)c(F)

SEQ ID NO:70: some part of RNA shown by SEQ ID NO:61 were modified with OMe and U24 was replaced with A(M).
ggga(M)a(M)gga(M)gga(M)a(M)g(M)u(F)g(M)c(F)a(M)c (F)aggg(M)g(M)a (M)u(F)g(M)g(M)u(F)g(M)u(F)c(F) gggu(F)g(M)c(F)a(M)c(F)

Here, n(M) represents ribose modified with OMe at the 2'-position, n(F) represents ribose modified with F at the 2'-position, n(H) represents deoxyribose, PEG2000 represents a 2000-Da polyethyleneglycol, PEG40k represents a branched 40 kDa polyethyleneglycol, PEG30k represents a 30 kDa polyethyleneglycol, C12 represents a C12 linker, and idT represents inverted dT.

An experiment on cell migration inhibition for pleiotrophin by the aptamer shown by SEQ ID NO:5 and altered forms thereof was performed. The experimental method was as described above, except that pleiotrophin was used instead of midkine. The aptamer concentration was 100 nM, and the inhibitory activity of the aptamer shown by SEQ ID NO:5 against midkine was taken as 100. As a result of the experiment, the inhibitory activity against pleiotrophin was 13 (Table 4-1). This is the mean for 6 measurements. In the altered forms, no remarkable inhibitory activity against pleiotrophin was observed.

The cell migration inhibitory activity of the aptamer shown by SEQ ID NO:35 against mouse midkine was examined. The experiment was the same as the above-described experimental method using human midkine. As a result of the experiment, the inhibitory activity % of this aptamer was 84%. Thus, this aptamer was found to possess an activity against mouse midkine equivalent to the inhibitory activity against human midkine.

Using tRNA (manufactured by Sigma), Thrombin-S, and HIV-S, which are unlikely to bind specifically to midkine, in place of the aptamers, a cell migration inhibition experiment for human midkine was performed as described above. Here, Thrombin-S is a DNA aptamer of t'ggttggtgtgtt gg'taaaaaaaaaaaaaaa (SEQ ID NO:74), and HIV-S is a DNA aptamer of g'tggtgggtgggtggg't (SEQ ID NO:75). Each "'" represents a phosphorothioate bond. The phosphorothioate bonds were added in order to increase the nuclease resistance. These RNAs were used at 500 nM. When the inhibitory activity of the aptamer shown by SEQ ID NO:45 against human midkine was taken as 100, the activity of tRNA was determined to be 28, Thrombin-S to be 0, and HIV-S to be 48. Hence, it was suggested that the aptamers prepared in the present study might be bound specifically to important sites associated with the cell migration activity of midkine.

The aptamer shown by SEQ ID NO:5, which was 77 nucleotides long, could be miniaturized to 39 nucleotides, without considerably reducing the activity (SEQ ID NO:61). The single-strand portion at the 5' end could not completely be deleted; it is postulated that this single-strand portion is involved in the formation of the steric structure of the aptamer. Although the G of this single-strand portion may be a F-modified nucleotide, it was found that the activity decreased in the case of OMe-modified nucleotides (SEQ ID NO:40-2, 54, 61-2). Meanwhile, even when the A was an OMe-modified nucleotide, the activity remained unchanged (SEQ ID NO:40-3). Even when some A-U base pairs were replaced with G-C base pairs in the stem on the 5' end side, the activity was not so much influenced (SEQ ID NO:46). Even when the A and G of this stem portion were replaced with an OMe-modified nucleotide, the activity was retained (SEQ ID NO:45-4). Even when the internal loop portion was replaced with a G-C stem structure by nucleotide substitution, the activity did not change (SEQ ID NO:63); however, when the single-strand portion was shortened, the activity decreased (SEQ ID NO:59). When the G and A of the internal loop were replaced with an OMe-modified nucleotide, the activity decreased (SEQ ID NO:45-3). When the loop portion was deprived of 1 nucleotide, the activity decreased (SEQ ID NO:47 to 49). Even when the G of the loop portion was replaced with an OMe-modified nucleotide, the activity was retained (SEQ ID NO:45-2).

From above, it was found that the activity of this aptamer obtained was not influenced even by substituting some 10 bases or changing the modification. It was also found that this aptamer bound specifically to midkine to inhibit the cell migration activity. Meanwhile, it was found that this aptamer also bound to the family protein pleiotrophin, but did not possess a remarkable cell migration inhibitory activity.

EXAMPLE 8

Inhibitory Effect of Aptamer on Organ Adhesion Using Mouse Postoperative Adhesion Formation Model The abdomen of a normal mouse is opened, and the peritoneum is incised with a surgical knife and the like, after which the internal organs are dried, and then the laparotomized part is sutured; within 5 days thereafter, organ adhesion is observable (Am J Obstet Gynecol 179, 438-443, 1998). It is reported that when midkine knockout mice were treated using this method for causing postoperative organ adhesion, postoperative organ adhesion did not occur (Biochemical and Biophysical Research Communication, 317, 108-113, 2004). Hence, using the mouse postoperative adhesion formation model, the postoperative organ adhesion preventing effect of the aptamer shown by SEQ ID NO:76 was investigated. Under anesthesia, an 8-week-old C57BL/6 mouse (female) was laparotomized, after which the peritoneum was wiped with absorbent cotton. Thereafter, an about 2 cm fissure was made in the peritoneum at five positions using scissors. After hemostasis with absorbent cotton for 10 minutes, the wound was sutured using a sewing needle and thread. After emergence, the aptamer shown by SEQ ID NO:76 was intraperitoneally administered at a dose of 1 mg/25 mL/kg. For a control group, saline containing 1 mM $MgCl_2$ was intraperitoneally administered at a dose of 25 mL/kg in the same manner. The administration took place once a day in a total of three times on postoperative day 0, day 1, and day 2, thereafter the animal was laparotomized under anesthesia on day 3, and the degree of organ adhesion to the wound was evaluated using the criteria shown below.

0: no adhesion
1: with adhesion, mild adhesion (mild)
2: with adhesion, moderate adhesion (moderate)
3: with adhesion, severe adhesion that cannot be detached even by pulling the organ at the adhering portion (severe)

The results are shown as the means and standard errors of scores of the degree of adhesion for 9 to 10 animals in each group (Table 5). As a result, the score was 3 in all animals in the group receiving physiological saline, whereas the mean score of the group receiving the aptamer shown by SEQ ID NO:76 was 2.4. In the group receiving the aptamer shown by SEQ ID NO:76, compared with the group receiving physiological saline, a statistically significant difference (p<0.05) was observed. For the statistical processing, Mann-Whitney U test was used. From the results above, it was demonstrated that the aptamer shown by SEQ ID NO:76 possessed a postoperative organ adhesion preventing activity.

The aptamer shown by SEQ ID NO:76 is as follows. SEQ ID NO:76: the RNA shown by SEQ ID NO:40 wherein all "A"s of the 5' end single-strand portion are modified with OMe, with cholesterol (Chol) added to the 5' end via a saturated hydrocarbon chain (C12) linker having 12 carbon atoms, and inverted dT (idT) added to the 3' end.

```
Chol-C12-ggga(M)ga(M)gga(M)ga(M)a(M)ga(M)gga(M)a
(M)gu(F)gu(F)gc(F)ac(F)aggggu(F)u(F)ggu(F)gu(F)c
(F)gggu(F)gc(F)au(F)ac(F)-idT
```

TABLE 5

Results of organ adhesion inhibition experiment using mouse model

| Administration | Score |
| --- | --- |
| Physiological saline | 3.0 +/− 0.0 |
| SEQ ID NO: 76 | 2.4 +/− 0.3* |

*p < 0.05 Mann-Whitney U test

This application is based on a patent application No. 2006-308482 filed in Japan (filing date: Nov. 14, 2006), the contents of which are incorporated in full herein by this reference.

The invention claimed is:

1. An aptamer possessing an inhibitory activity against midkine, which is either (a) or (b) below:
   (a) an aptamer comprising a nucleotide sequence selected from SEQ ID NOs: 20 and 67 (with the provision that the uracil may be thymine), wherein the nucleotides contained in the aptamer are such that,
      (i) the 2'-positions of the pyrimidine nucleotides, whether identical or different, are fluorine atoms or substituted by atoms or groups selected from the group consisting of hydrogen atoms, hydroxy groups and methoxy groups, and
      (ii) the 2'-positions of the purine nucleotides, whether identical or different, are hydroxy groups or substituted by atoms or groups selected from the group consisting of hydrogen atoms, methoxy groups and fluorine atoms;
   (b) an aptamer comprising a nucleotide sequence selected from SEQ ID NOs: 20 and 67 (with the provision that the uracil may be thymine), wherein one to three nucleotides are substituted, deleted, inserted or added, wherein the nucleotides contained in the aptamer are such that,
      (i) the 2'-positions of the pyrimidine nucleotides, whether identical or different, are fluorine atoms or substituted by atoms or groups selected from the group consisting of hydrogen atoms, hydroxy groups and methoxy groups, and
      (ii) the 2'-positions of the purine nucleotides, whether identical or different, are hydroxy groups or substituted by atoms or groups selected from the group consisting of hydrogen atoms, methoxy groups and fluorine atoms.

2. The aptamer of claim 1, wherein substitution, deletion, insertion and/or addition of one to three nucleotides is acceptable in the single-strand region, first stem region, internal loop region, second stem region, and hairpin loop region.

3. The aptamer of claim 1, which is altered by adding to an end thereof a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance or biotin.

4. A complex comprising a functional substance and the aptamer of claim 1 or 2.

5. The complex of claim 4, wherein the functional substance is an affinity substance, a substance for labeling, an enzyme, a drug delivery vehicle or a drug.

6. A pharmaceutical drug comprising the aptamer of claim 1 or 2.

7. A cell migration inhibitor comprising the aptamer of claim 1 or 2.

8. A diagnostic reagent comprising the aptamer of claim 1 or 2.

9. A labeling agent comprising the aptamer of claim 1.

10. A method of detecting midkine using the aptamer of claim 1.

11. A pharmaceutical drug comprising the complex of claim 4.

12. A cell migration inhibitor comprising the complex of claim 4.

13. A diagnostic reagent comprising the complex of claim 4.

14. A labeling agent comprising the complex of claim 4.

15. A method of detecting midkine using the complex of claim 4.

* * * * *